(12) United States Patent
Bahl et al.

(10) Patent No.: US 11,791,049 B2
(45) Date of Patent: Oct. 17, 2023

(54) METHODS AND SYSTEMS FOR DETECTING INTRAVASCULAR DEVICE FAILURE

(71) Applicant: A Little Cold Gel, LLC, Bloomfield Hills, MI (US)

(72) Inventors: Amit Bahl, Bloomfield Hills, MI (US); Steven Johnson, Claremont, CA (US)

(73) Assignee: A Little Cold Gel, LLC, Bloomfield Hills, MI (US)

( * ) Notice: Subject to any disclaimer, the term of this patent is extended or adjusted under 35 U.S.C. 154(b) by 0 days.

(21) Appl. No.: 17/980,067

(22) Filed: Nov. 3, 2022

(65) Prior Publication Data
US 2023/0138206 A1    May 4, 2023

Related U.S. Application Data

(60) Provisional application No. 63/274,998, filed on Nov. 3, 2021.

(51) Int. Cl.
*G16H 50/20* (2018.01)
*A61M 5/168* (2006.01)
(Continued)

(52) U.S. Cl.
CPC ........... *G16H 50/20* (2018.01); *A61B 8/0841* (2013.01); *A61B 8/5223* (2013.01);
(Continued)

(58) Field of Classification Search
CPC ........ G16H 50/20; G16H 50/70; G16H 20/17; G16H 30/20; G16H 30/40; G16H 40/67;
(Continued)

(56) References Cited

U.S. PATENT DOCUMENTS

| 9,320,872 B2 | 4/2016 | Urmey |
| 9,888,337 B1 * | 2/2018 | Zalewski ............. H04W 76/14 |

(Continued)

FOREIGN PATENT DOCUMENTS

| CA | 3056498 | 9/2018 |
| EP | 1545315 | 6/2005 |
| JP | 6827499 B | 2/2021 |

OTHER PUBLICATIONS

Bahl, Amit et al., PLOS ONE, "Early recognition of peripheral intravenous catheter failure using serial ultrasonographic assessments", Jun. 16, 2021, pp. 1-12.
(Continued)

*Primary Examiner* — Sanjay Cattungal
(74) *Attorney, Agent, or Firm* — Bradley Arant Boult Cummings LLP

(57) ABSTRACT

A diagnostic system to aid in diagnosing conditions underneath a subject's skin that predict intravascular device failure is provided. The diagnostic system includes an ultrasound unit that uses ultrasonic energy to obtain images underneath the subject's skin surrounding the insertion site of an intravascular device. The ultrasound unit is in electronic communication with a computing device that collects and stores data generated by the ultrasound unit. The computing device utilizes machine learning or artificial intelligence techniques to identify conditions underneath the subject's skin that predict intravascular device failure, and through a user interface, indicates to the user that subcutaneous conditions predictive of intravascular device failure are present.

13 Claims, 9 Drawing Sheets

(51) Int. Cl.
*A61B 8/08* (2006.01)
*A61B 90/00* (2016.01)

(52) U.S. Cl.
CPC ....... *A61M 5/16836* (2013.01); *A61B 8/0891* (2013.01); *A61B 2090/378* (2016.02); *A61M 2205/3375* (2013.01)

(58) Field of Classification Search
CPC .... G16H 50/30; A61B 8/0841; A61B 8/5223; A61B 8/0891; A61B 2090/378; A61B 8/5207; A61B 8/06; A61B 8/0883; A61B 8/085; A61B 8/12; A61M 5/16836; A61M 2205/3375; A61M 2005/1588
See application file for complete search history.

(56) References Cited

U.S. PATENT DOCUMENTS

| | | | | |
|---|---|---|---|---|
| 9,911,290 | B1* | 3/2018 | Zalewski | G06Q 20/327 |
| 10,372,894 | B2* | 8/2019 | Kim | G06F 21/32 |
| 10,751,508 | B2 | 8/2020 | McKinnon et al. | |
| 10,944,728 | B2* | 3/2021 | Wiener | H04L 63/0428 |
| 11,576,677 | B2* | 2/2023 | Shelton, IV | H01Q 1/22 |
| 11,659,023 | B2* | 5/2023 | Shelton, IV | G16H 40/20 |
| | | | | 709/227 |
| 2005/0245858 | A1 | 11/2005 | Miesel et al. | |
| 2007/0258626 | A1* | 11/2007 | Reiner | G16H 40/20 |
| | | | | 340/5.82 |
| 2012/0232434 | A1 | 9/2012 | Nita et al. | |
| 2014/0355381 | A1* | 12/2014 | Lal | G01N 29/022 |
| | | | | 327/356 |
| 2015/0182118 | A1* | 7/2015 | Bradbury | A61P 27/02 |
| | | | | 600/431 |
| 2016/0238651 | A1* | 8/2016 | An | G01R 19/15 |
| 2017/0104861 | A1* | 4/2017 | Kang | G06V 40/172 |
| 2017/0244655 | A1* | 8/2017 | Moon | H04L 12/185 |
| 2017/0318141 | A1* | 11/2017 | Gerace | H04M 1/27475 |
| 2018/0011590 | A1* | 1/2018 | Lee | G06V 40/13 |
| 2018/0144243 | A1* | 5/2018 | Hsieh | G06F 11/30 |
| 2018/0144465 | A1* | 5/2018 | Hsieh | G06N 3/08 |
| 2018/0247039 | A1* | 8/2018 | Yoon | G06F 21/84 |
| 2019/0011921 | A1* | 1/2019 | Wang | G05D 1/106 |
| 2019/0132436 | A1* | 5/2019 | Jang | H04M 1/72415 |
| 2019/0259491 | A1* | 8/2019 | Bronkalla | G06F 16/58 |
| 2019/0384383 | A1* | 12/2019 | Lee | G06F 3/011 |
| 2020/0034785 | A1* | 1/2020 | Romano | B65F 3/14 |
| 2020/0035217 | A1* | 1/2020 | Chae | G10L 13/00 |
| 2020/0187870 | A1 | 6/2020 | Bosque | |
| 2020/0190963 | A1* | 6/2020 | Gooneratne | E21B 44/00 |
| 2020/0226422 | A1 | 7/2020 | Li et al. | |
| 2020/0226898 | A1* | 7/2020 | Kinoshita | G08B 13/19697 |
| 2020/0234812 | A1 | 7/2020 | Willybiro et al. | |
| 2021/0088867 | A1* | 3/2021 | Nagel | G01N 21/8851 |
| 2021/0136450 | A1* | 5/2021 | Kim | H04N 21/435 |
| 2021/0157312 | A1* | 5/2021 | Cella | G01M 13/045 |
| 2021/0369246 | A1* | 12/2021 | Baba | A61B 8/461 |
| 2022/0108262 | A1* | 4/2022 | Cella | G06Q 10/063118 |
| 2022/0157139 | A1* | 5/2022 | Subramany | G08B 13/19663 |
| 2022/0215948 | A1* | 7/2022 | Bardot | G16H 40/67 |
| 2022/0361840 | A1* | 11/2022 | Matsumoto | A61B 8/0891 |
| 2023/0044399 | A1* | 2/2023 | Shochat | A61B 5/489 |
| 2023/0138206 | A1* | 5/2023 | Bahl | A61B 8/085 |
| | | | | 604/508 |
| 2023/0157552 | A1* | 5/2023 | Thuering | A61B 5/0205 |
| | | | | 600/301 |

OTHER PUBLICATIONS

Mielke, Nicholas et al., The Journal of Vascular Access, "A prospective sonographic evaluation of peripheral intravenous catheter associated thrombophlebitis," 2021, pp. 1-10.
Early Detection of IV Infiltration and Extravasation, ivWatch IV Monitoring, pp. 1-8, https://www.ivwatch.com, accessed on Nov. 11, 2022.
I.V. House, pp. 1-10, https://www.ivhouse.com, accessed on Nov. 11, 2022.
Medline, Medline IV Start Kits with Chloraprep, pp. 1-2; https://punchout.medline.com/product/IV-Start-Kits-with-Chloraprep/IV-Start-Kits/Z05-PF06668?ques_3, accessed on Nov. 11, 2022.
Bicen, A. Ozan et al., Hematology and Hemostasis, "Toward Non-Invasive and Automatic Intravenous Infiltration Detection: Evaluation of Bioimpedance and Skin Strain in a Pig Model," vol. 6, Apr. 3, 2018. pp. 1-7, https://ieeexplore.ieee.org/stamp/stamp.jsp?arnumber=8330755.
Alley, Matthew S. et al., "Wireless Application in Intravenous Infiltration Detection System," 2008, pp. 1-10, https://www.ncbi.nlm.nih.gov/pmc/articles/PMC2630506.
Kanno, Chiho et al., "Development of an Algorithm using Ultrasonography-Assisted Peripheral Intravenous Catheter Placement for Reducing Catheter Failure", Drug Discoveries & Therapeutics, 2020, 14(1), pp. 27-34.
International Search Report and Written Opinion dated Feb. 9, 2023 of corresponding International Patent Application No. PCT/US22/48819.

\* cited by examiner

Short axis without thrombus

Short axis with thrombus

Long axis without thrombus

Long axis with thrombus

METHODS AND SYSTEMS FOR DETECTING INTRAVASCULAR DEVICE FAILURE

REFERENCE TO RELATED APPLICATIONS

This application claims priority to Provisional Patent Application U.S. Ser. No. 63/274,998, entitled "Peripheral IV Catheter Failure Detection" and filed on Nov. 3, 2021, which is fully incorporated herein by reference.

BACKGROUND AND SUMMARY

Peripheral intravenous vascular catheters (PIVCs) are the most used intravenous devices in hospitalized patients and are instrumental in delivering patient care within hospitals and care facilities. Over 300 million PIVCs are used yearly in the United States. PIVCs help to quickly and efficiently provide medication, nutrition, and fluids to patients through the bloodstream by being inserted into small peripheral veins.

Although commonly used, PIVCs have a high overall failure rate of 35%-50%, which leads to patient discomfort, premature removal, and replacement. The most common site for a PIVC placement is either at the forearm, the back of the hand or the inner part of the mid-arm called the antecubital fossa. Placement of the PIVC is completed by a practitioner (physician, nurse, or technician) and is performed by visual and tactile assessment to find the most accessible vein. Once the most accessible vein is located, and the equivalent catheter size is determined, then insertion of the PIVC is performed. Practitioners aim to have success with the first PIVC insertion because additional insertions may lead to pain and discomfort for the patient, complications to the PIVC insertion site, and additional costs to the healthcare system. Once PIVC placement is confirmed, it is important to continuously check the PIVC insertion site.

According to the Infusion Nursing Society (INS) Infusion Therapy Standards of Practice, it is recommended to check PIVC insertion sites at different frequencies depending on the patient and the severity of the treatment. PIVC checks should be done every 1 to 2 hours for critically ill and sedated patients, hourly for neonatal and pediatric patients, and more often for patients receiving blister agents, also known as vesicant medications. For other patients with a PIVC, inspection should be performed at least every four hours. As a best practice, practitioners will also attach an extension line to the PIVC to help minimize risk of contamination, movement, and complications. Much emphasis is placed on checking and assessing the insertion site due to PIVC's high overall failure rate of 35%-50%. The most common complications are infection, catheter position/migration, occlusion, phlebitis (skin irritation, tenderness, swelling, and pain), and infiltration/extravasation (when nonvesicant or vesicant IV fluid leaks into the surrounding tissue due to the IV catheter going through or coming out of the vein).

External visual and tactile site assessment performed by an individual, such as a nurse, is the standard approach to assess intravascular catheter sites. Nurses will generally observe the external portion of the intravascular device site for various complications. However, these assessments are very limited, and as the presence of complications generally equates to the need for catheter removal, once the complication is externally evident, little can be done to reverse course. Limited other tools exist on the market to help improve the meaningfulness of the site assessment.

Accordingly, there is a need for methods and systems that reliably monitor changes occurring at the subcutaneous level in patients with intravascular devices, such as PIVCs, and predict intravascular device failure before external evidence of failure. Early recognition of intravascular device failure can allow clinicians to better plan for a patient's vascular access needs and prevent delays in care, such as longer hospital lengths of stay, delays in administration of critical medications, unnecessary needlesticks if appropriate personnel are unavailable at the time device failure is recognized, and patient dissatisfaction. Notably, longer hospital stays are associated with iatrogenic complications, such as bloodstream infections and higher mortality rates.

In at least one aspect, the system according to the present disclosure provides a system to aid in diagnosing conditions and alterations underneath a subject's skin that predict intravascular device failure. In particular, the system includes an ultrasound unit that uses ultrasonic energy to obtain images underneath the subject's skin surrounding the insertion site of an intravascular device. The ultrasound unit is in electronic communication with a computing device that collects and stores data generated by the ultrasound unit. Advantageously, the computing device applies artificial intelligence to identify relevant subcutaneous or intravascular alterations underneath the subject's skin surrounding the area of insertion of an intravascular device that predict intravascular device failure. Through a user interface, the device indicates to the user that subcutaneous alterations predictive of intravascular device failure are present.

In another aspect, an ultrasound system is provided that includes an ultrasound unit and a computing device. The ultrasound unit is configured to utilize ultrasonic energy to obtain data characterizing the area underneath the subject's skin surrounding the insertion site of an intravascular device. The computing device is in electronic communication with the ultrasound unit and is configured to execute a method whereby it receives and stores the data obtained by the ultrasound unit, including images and measurements of subcutaneous features surrounding the insertion site of an intravascular device, utilizes machine learning or artificial intelligence techniques to process the data; and provides information indicating to the user whether subcutaneous or intravascular alterations are present that predict intravascular device failure, or information indicating a physical correction or corrections that promote optimal placement of the intravascular device, thus minimizing device failure.

In another aspect, a method for diagnosing alterations underneath a subject's skin that predict intravascular device failure. The method includes steps of applying ultrasonic energy from an ultrasound unit to an area under the subject's skin to generate data characterizing the area underneath subject's skin when placed over an insertion site of an intravascular device, collecting and storing data generated by the ultrasound unit, such data including at least one of images or measurements of the area underneath the subject's skin near the insertion site of the intravascular device, applying one or more trained machine learning or artificial intelligence computer-implemented methods to process the data collected and stored, and providing an indication to a user, the indication including at least one of an indication of alterations underneath the subject's skin that predict intravascular device failure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

For a further understanding of the nature, objects, and advantages of the present disclosure, reference should be made to the following detailed description, read in conjunction with the following drawings, wherein like reference numerals denote like elements and wherein:

FIG. 6A illustrates the vein diameter (short axis). FIG. 6B illustrates the vein wall width (short axis). FIG. 6C illustrates the distance of the distal catheter tip to vein wall (long axis). FIG. 6D illustrates the length of the catheter in the vein (long axis). FIG. 6E illustrates the insertion angle (left) and the angle of distal tip to vessel wall (right) (long axis). FIG. 6F illustrates the degree of kink/bend (long axis).

DETAILED DESCRIPTION

Figure 1:
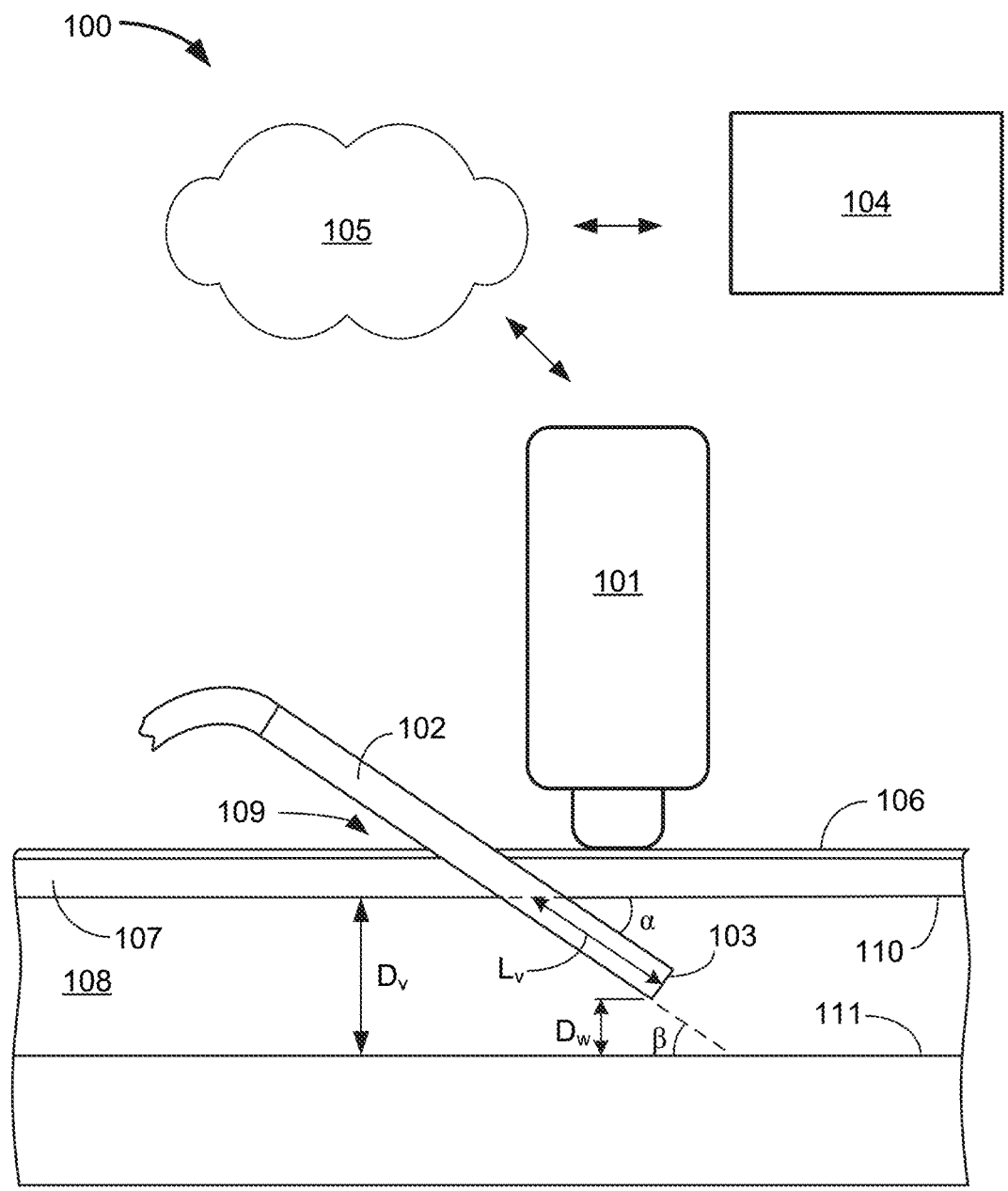
FIG. 1 illustrates a system according to an exemplary embodiment of the present disclosure.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terms "about" and "approximately" shall generally mean an acceptable degree of error or variation for the quantity measured given the nature or precision of the measurements. Numerical quantities given in this description are approximate unless stated otherwise, meaning that the term "about" or "approximately" can be inferred when not expressly stated.

The terminology used herein is for the purpose of describing particular embodiments only and is not intended to be limiting. As used herein, the singular forms "a", "an" and "the" are intended to include the plural forms as well (i.e., at least one of whatever the article modifies), unless the context clearly indicates otherwise.

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object (one or more modules of computer program instructions). Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

When a computing device is described as performing an action or method step, it is understood that the computing device is operable to perform the action or method step typically by executing one or more lines of source code. The actions or method steps can be encoded onto non-transitory memory (e.g., hard drives, optical drive, flash drives, and the like).

The term "computing device" generally refers to any device that can perform at least one function, including communicating with another computing device. In a refinement, a computing device includes a central processing unit that can execute program steps and memory for storing data and a program code.

The term "artificial intelligence" refers to a computer system with intelligent functions, such as inference and determination, including a knowledge base part configured to accumulate knowledge, and an inference unit that derives conclusions from the accumulated knowledge, and includes those having a learning function that automatically constructs a knowledge base and corrects erroneous knowledge. As specific examples, machine-learning, artificial neural networks, expert system, case base reasoning, Bayesian network, fuzzy control, evolutionary calculation, are included, and may be combined with generation of an inference rule of an expert, such as an ACT-R, through a neural network or a generation rule based on statistical learning.

The term "machine-learning" is one of artificial intelligence and is a technology and a technique that attempts to realize a function similar to a learning ability that a human naturally performs, and also is a technique that allows a computer to learn without explicitly instructing through a program.

The term "deep learning" refers to machine-learning having a multilayer perceptron having at least an input layer and an intermediate layer of one or more layers and an output layer (machine-learning that is referred to as a deep neural network).

The term "neural network" refers to a machine learning model that can be trained with training input to approximate unknown functions. In one embodiment, neural networks include a model of interconnected digital neurons that communicate and learn to approximate complex functions and generate outputs based on a plurality of inputs provided to the model. Embodiments, variations, and refinements of the neural networks and the operations described in this specification can be implemented in digital electronic circuitry, or in computer software, firmware, or hardware, including the structures disclosed in this specification and their structural equivalents, or in combinations of one or more of them.

Throughout this application, where publications are referenced, the disclosures of these publications in their entireties are hereby incorporated by reference into this application to more fully describe the state of the art to which this disclosure pertains.

The present disclosure provides improved methods and systems for detecting intravascular catheter failure, for example, peripheral IV catheter failure. In some embodiments, the present disclosure utilizes ultrasound imaging systems and machine learning or artificial intelligence technology to determine whether ultrasound images and measurements of the area underneath the skin of a subject that surrounds the area of insertion of an intravascular device indicate subcutaneous or intravascular alterations that predict device failure. The methods and systems of the present disclosure allow for the identification of impending intravascular device failure much earlier than devices currently on the market and before such failure becomes clinically apparent. This allows medical teams to strategize and develop vascular access plans to avoid delays or interrupted treatment and recruit the appropriately qualified medical professional to place the catheter based upon the patient's vascular needs.

FIG. 1 illustrates a system 100 according to an exemplary embodiment of the present disclosure. The system 100 comprises an ultrasound unit 101 that uses ultrasonic energy to obtain images underneath skin 106 of a subject over an insertion site 109 of an intravascular device, in this example, an intravascular catheter 102. As used herein, the term "insertion site" may refer to the location where the intravascular device is inserted into the subject's skin, the area surrounding the location of insertion of the intravascular device, the internal pathway of the intravascular device, the area within the vasculature surrounding the intravascular device, or any combination of the foregoing. The catheter 102 is inserted in the subject's vasculature, as further discussed herein. The term "subject," as used herein, refers to any animal, including mammals, such as mice, rats, other rodents, rabbits, dogs, cats, swine, cattle, sheep, horses, or primates, and humans. The term may specify male or female or both.

In the illustrated embodiment, the catheter 102 has been inserted through the subject's skin 106 and subcutaneous tissue 107 into a vein 108 of the subject. The vein 108 has a diameter Dv, and the catheter 102 has been inserted into the vein 108 at an insertion angle "a" to the inner vein wall 110. A length Lv of the catheter 102 is within the vein 108.

The catheter 102 has a distal tip 103 that is an orthogonal distance Dw from a deep wall 111 of the vein 108. The catheter 102 is disposed at an angle β to the deep wall 111.

In some embodiments, instead of the catheter 102 as depicted, the intravascular device may be one of: peripheral intravenous catheter, arterial catheter, peripherally inserted central catheter (PICC), midline catheter, extended dwell catheter, central venous catheter (CVC), hemodialysis catheter, ECMO cannulation, transvenous pacemaker, Reboa catheter, or intra-aortic balloon pump. In one embodiment, the intravascular device is a peripheral intravenous catheter.

The ultrasound unit 101 is in electronic communication with at least one computing device 104 that collects and stores data generated by the ultrasound unit 101. In the illustrated embodiment, the ultrasound unit 101 sends raw image data (not shown) to the computing device 104 over a network 105. The network 105 may be of any type of network or networks known in the art or future-developed, such as the internet backbone, Ethernet, Wifi, WiMax, broadband over power line, coaxial cable, and the like. The network 105 may be any combination of hardware, software, or both. Further, the network 105 could be resident in a sensor (not shown) housing both the ultrasound unit 101 and the computing device 104.

The computing device 104 utilizes artificial intelligence techniques, such as machine learning, to identify alterations underneath the subject's skin that predict intravascular device failure, and through a user interface (not shown), indicates to the user that subcutaneous alterations predictive of intravascular device failure are present. In some embodiments, cloud computing and storage can be used. In further embodiments, edge computing can be used. Characteristically, computing device 104 is a trained computing device.

Figure 2:
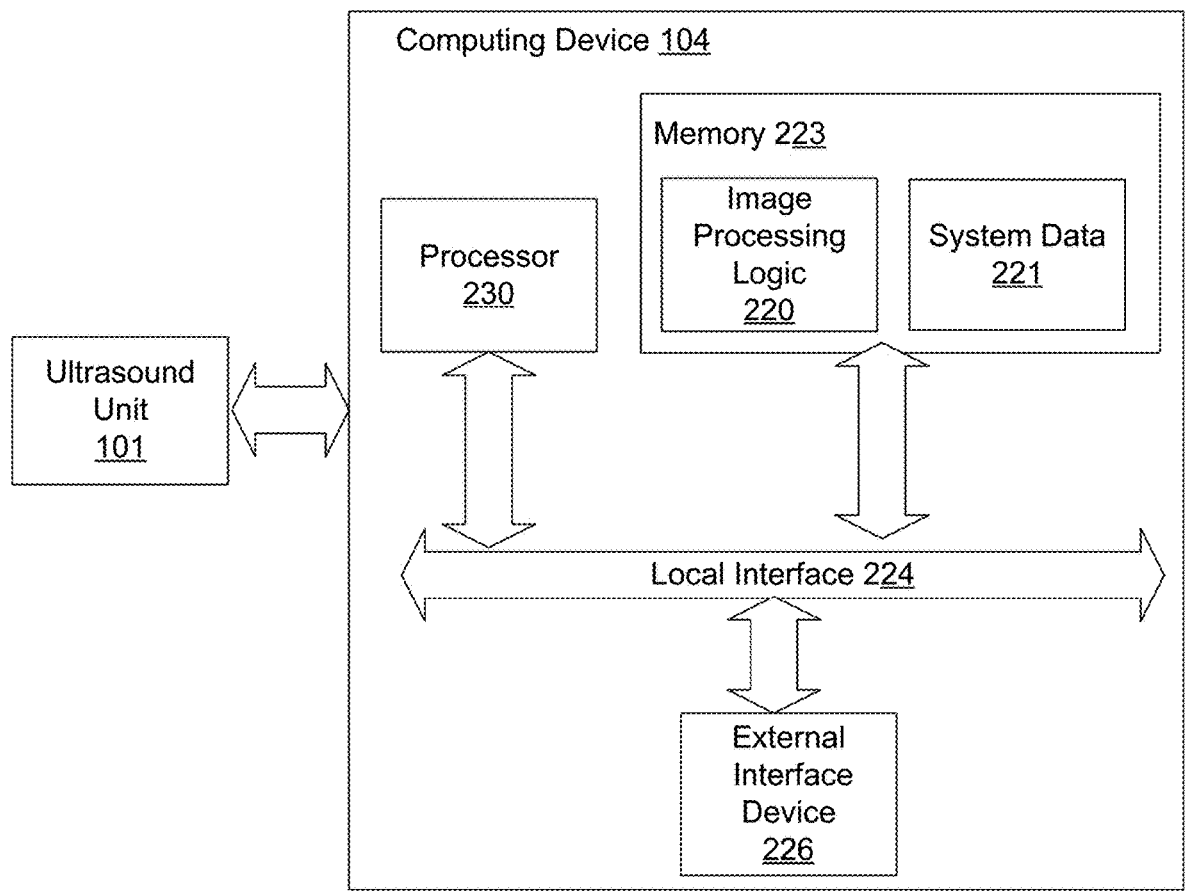
FIG. 2 depicts an exemplary ultrasound unit and computing device according to an embodiment of the present disclosure.

FIG. 2 depicts an exemplary ultrasound unit 101 and computing device 104 according to an embodiment of the present disclosure. The computing device 104 comprises image processing logic 220, such as ultrasound image processing logic, and system data 221. In the exemplary computing device 104, the image processing logic 220 and the system data 221 are shown as stored in memory 223. The image processing logic 220 and system data 221 may be implemented in hardware, software, or a combination of hardware and software.

The computing device 104 also includes a processor 230, which comprises a digital processor or other type of circuitry configured to run the image processing logic 220 by processing the image processing logic 220, as applicable. The processor 230 communicates to and drives the other elements within the computing device 104 via a local interface 224, which can include one or more buses. When stored in memory 223, the image processing logic 220 and the system data 221 can be stored and transported on any computer-readable medium for use by or in connection with a logic circuitry, processor, an instruction execution system, apparatus, or device, such as a computer-based system, processor-containing system, or other system that can fetch the instructions from the instruction execution system, apparatus, or device and execute the instructions. As used herein, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

In some embodiments, the system data 221 includes one or both of images and measurements taken by the ultrasound unit 101 of the area underneath the subject's skin near the insertion site of the intravascular device. The images and measurements taken by the ultrasound unit 101 capture both intravascular and extravascular changes underneath the subject's skin. For example, in one embodiment, the system data 221 may include images of the intravascular device, such as the intravascular catheter 102. In another embodiment, the system data 221 may include images of a distance from the intravascular device to a wall of vasculature in which it is inserted. In still another embodiment, the system data 221 may include measurements of a distance between the intravascular device and the wall of vasculature in which it is inserted. In yet other embodiments, the system data 221 may include measurements of a ratio of intravascular device diameter to vascular diameter. In further embodiments, the system data 221 may include measurements of a length of intravascular device that resides within the vasculature, such as length Lv depicted in FIG. 1. In still further embodiments, the system data 221 may include images of an area inside the vasculature in which the intravascular device is inserted. In yet further embodiments, the system data 221 may include images of an area surrounding the vasculature in which the intravascular device is inserted. In other embodiments, the system data 221 may include images and/or measurements of the angle of insertion of the intravascular device. For example, the system data 221 may include images and/or measurements of the angle of the intravascular device against the shallow wall of the vein, such as insertion angle "a" shown in FIG. 1. In further embodiments, the system data 221 may include images and/or measurements of the angle of the distal tip of the intravascular device against the deep wall of the vein, such as angle β illustrated in FIG. 1. In still further embodiments, the system data 221 may include images and/or measurements of the vein wall thickness. In yet further embodiments, the system data 221 may include images and/or measurements of the distance of the catheter tip to the deep wall of the vein, such as orthogonal distance Dw shown in FIG. 1. In further embodiments, the system data 221 may include images and/or measurements of the degree of catheter kinking. In still further embodiments, the system data 221 may include images and/or measurements of the size of thrombus formation. In other embodiments, the system data 221 may include images/measurements of subcutaneous edema formation. As will be appreciated by those of ordinary skill in the art, the images and/or measurements taken by the ultrasound unit 101 may vary depending on the type of intravascular device used in the subject.

The image processing logic 220, such as ultrasound image processing logic, executes the processes described further herein.

An external interface device 226 may connect to and communicate with an input device, for example, a keyboard, a switch, a mouse, and/or other type of interface, which can be used to input data from a user of the system 100. The external interface device 226 may also communicate with or include a display device (not shown) that can be used to display data to the user. The external interface device 226 may also or alternatively communicate with or include a personal digital assistant (PDA), computer tablet device, laptop, portable or non-portable computer, cellular or mobile phone, or the like. The external interface device may also or alternatively communicate with or comprise a non-personal computer, for example, a server, embedded computer, FPGA, microprocessor, or the like.

The external interface device 226 is shown as part of the computing device 104 in the exemplary embodiment of FIG. 2. In other embodiments, the external interface device 226 may be outside of the computing device 104.

In some embodiments, the ultrasound unit 101 may be a handheld probe configured to acquire ultrasound images and measurements of the area underneath the subject's skin surrounding the insertion site of the intravascular device. The handheld probe is in electronic communication with a computing device 104 that executes the method of receiving and storing the data obtained by the ultrasound unit, including images and measurements of subcutaneous features surrounding the insertion site of an intravascular device, utilizing machine learning or artificial intelligence techniques to process the data; and providing information indicating to the user whether subcutaneous alterations are present that predict intravascular device failure, or information indicating a physical correction or corrections that promote optimal placement of the intravascular device, thus minimizing device failure.

In further embodiments, the computing device 104 utilizes a deep learning network or a convolutional neural network that may receive ultrasound training data from a number of ultrasound units composed of images, measurements, and information as to whether the particular subject from which the ultrasound training data were obtained experienced intravascular device failure. In this step, the ultrasound training data may be used to train the system (e.g., train the artificial intelligence computer-implemented methods) to predict intravascular device failure. After training, the computing device 104 can be referred to as a trained computing device. The deep learning network or a convolutional neural network is configured to develop knowledge of both the ultrasound training data and subject-acquired ultrasound data based on the ultrasound training data received. The ultrasound training data may further be received from a number of subjects that experienced intravascular device failure and a number of subjects that did not experience intravascular device failure. The neural network may use these ultrasound training data to acquire knowledge of subcutaneous features that predict intravascular device failure. The neural network may then utilize this knowledge to identify the presence of such subcutaneous features in ultrasound data that it obtains from the ultrasound unit, and may indicate to the user, through a user interface, that intravascular device failure is predicted to occur in the subject from which the ultrasound data were obtained.

In some embodiments, the ultrasound training data includes at least one of images or measurements of the area underneath the subject's skin surrounding the insertion site of the intravascular device, such as those described above and stored within the system data, and an indication, the indication including at least one of intravascular device failure or intravascular device success paired with images or measurements received from test subjects. The ultrasound training data can be received from a plurality of subjects, including subjects that experience intravascular device failure and subjects that experience successful intravascular device operation. Advantageously, the knowledge developed by the deep learning or convolutional neural network includes at least one of information permitting classification of types of alterations underneath the subject's skin that lead to intravascular device failure, information permitting classification of optimal placement of a device within a subject's intravascular space, or information permitting classification of an optimal rotation or angle of the intravascular device within the subject's intravascular space.

In further embodiments, the neural network may utilize the knowledge that it acquires from the ultrasound training data to identify and indicate to the user through a user interface, physical corrections that may be made by the user that promote the optimal placement of the intravascular device and minimize the potential for device failure. For example, the distal tip of the intravascular device may cause irritation of the intimal wall of the vein and induce an inflammatory response resulting in subcutaneous edema and failure of the intravascular device. In one embodiment, the methods and systems of the present disclosure may detect this non-optimal positioning of the intravascular device and provide a physical correction to the user, such as a recommendation to rotate the intravascular device so that the tip position changes subdue the inflammatory response or a recommendation to adjust the positioning of the intravascular device so as to pull it away from the intimal wall. As another example, the methods and systems of the present disclosure may detect peri-catheter thrombosis that is developing within the subject and provide a physical correction to the user, such as a recommendation to flush the intravascular device with saline to alleviate a pending occlusion.

Figure 3:
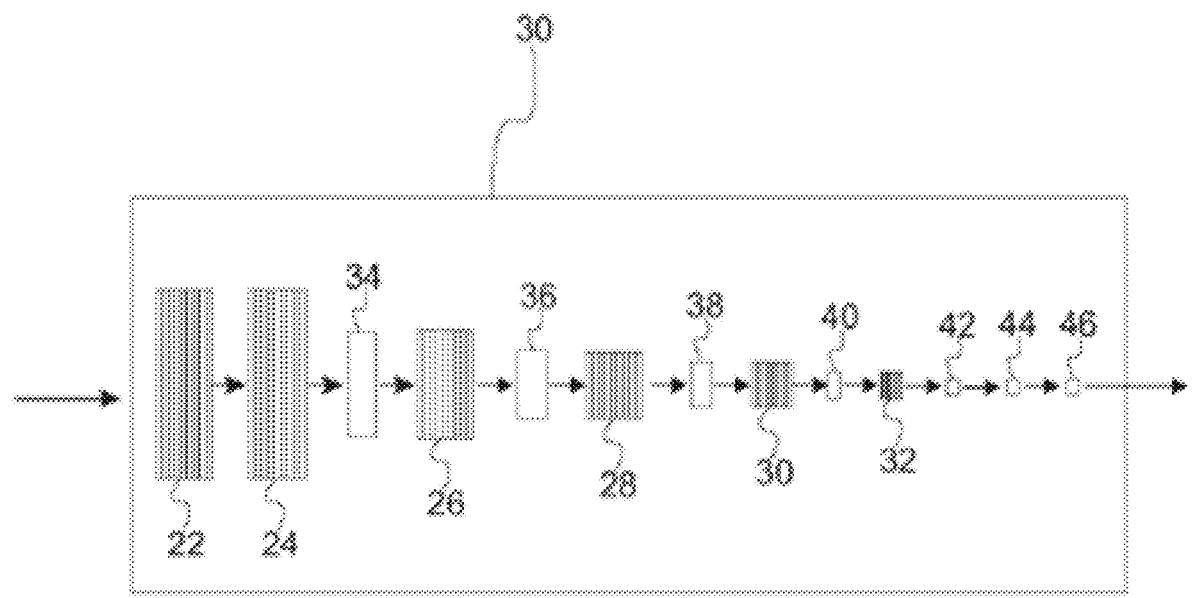
FIG. 3 depicts an idealized schematic illustration of a convolutional neural network executed by a computing system.

FIG. 3 depicts an idealized schematic illustration of a convolutional neural network executed by computing system 100. It should be appreciated that any deep convolutional neural network that operates on pre-processed input can be utilized. The convolutional network can include convolutional layers, pooling layers, fully connected layers, normalization layers, a global mean layer, and a batch-normalization layer. For example, convolutional neural network 20 receives data from ultrasound device 101. Convolutional neural network 30 includes a plurality of convolution layers 22, 24, 26, 28, 30, and 32 as well as pooling layers 34, 36, 38, 40, and 42. The pooling layers can be max-pooling layer or a mean pooling layer. In another embodiment, convolutional layers with a stride size greater than 1 may be used. FIG. 3 also depicts a network with global mean layer 44 and batch normalization layer 46. It should be appreciated that the present embodiment is not limited to by number of convolutional layers, pooling layers, fully connected layers, normalization layers, and sublayers therein.

Figure 4:
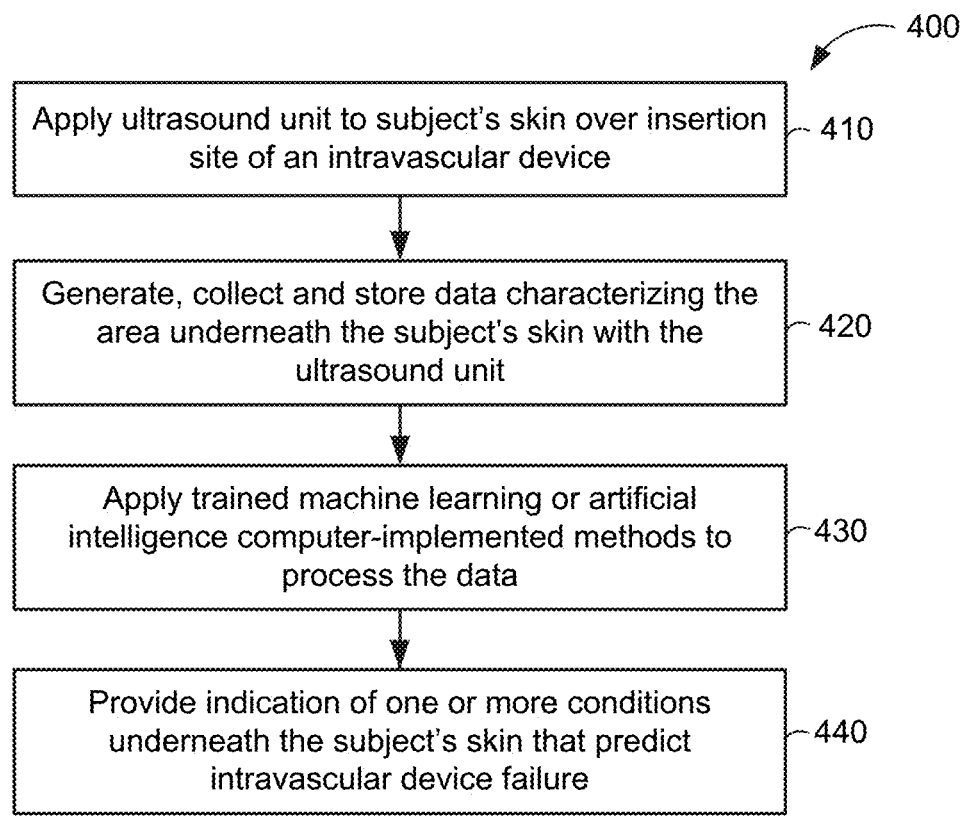
FIG. 4 depicts an exemplary method of diagnosing conditions underneath a subject's skin that predict intravascular device failure, according to an embodiment of the present disclosure.

FIG. 4 depicts an exemplary method 400 of diagnosing conditions underneath a subject's skin that predict intravascular device failure, according to an embodiment of the present disclosure. In step 410 of the method, ultrasonic energy is applied to an area of the subject's skin over the insertion site of an intravascular device with the ultrasound unit 101 (FIG. 1). The area to which the ultrasonic energy is applied should be sufficiently large enough to generate images of the entire insertion site of the intravascular device. In some embodiments, the area to which the ultrasonic energy is applied (or the scan area) is about 5 centimeters in width and 10 centimeters in length.

In one embodiment of the method, a series of cine clips of the scan area is recorded. In some embodiments, the length of the cine clips is about 3 seconds to about 60 seconds. For example, in one embodiment, the length of the cine clips is about 5 seconds. In another embodiment, the length of the cine clips is about 10 seconds. In still another embodiment, the length of the cine clips is about 30 seconds. In yet another embodiment, the length of the cine clips is about 60 seconds. In further embodiments of the method, real time video of the scan area can be recorded. For example, real time video generated by the ultrasound unit 101 can be displayed to a user in real time on a portable electronic device, such as a tablet. In still further embodiments, any video generated by the ultrasound unit 101 can be loaded as an application programming interface (API) and displayed in real time. The artificial intelligence computer-implemented methods described herein may indicate to the user when there is sufficient data from the cine clips and/or real time video to make a determination as to whether a failure of the intravascular device is predicted to occur.

In step 420 of the method, data characterizing the area underneath the subject's skin is generated by the ultrasound unit 101 and collected and stored in the ultrasound unit 101 or computing device 104 (FIG. 1). In one embodiment, the data collected and stored includes one or more of the following: images of the intravascular device; images of a distance from the intravascular device to a wall of vasculature in which it is inserted; measurements of a distance between the intravascular device and the wall of vasculature in which it is inserted; measurements of a ratio of intravascular device diameter to vascular diameter; measurements of a length of intravascular device that resides within the vasculature; images of an area inside the vasculature in which the intravascular device is inserted; images of an area surrounding the vasculature in which the intravascular device is inserted; images and/or measurements of the angle of insertion of the intravascular device; images and/or measurements of the angle of distal tip of the intravascular device against the vessel wall; images and/or measurements of the vein wall thickness; images and/or measurements of the distance of the catheter tip to the deep wall of the vein; images and/or measurements of the degree of catheter kinking; images and/or measurements of the size of thrombus formation; and images/measurements of subcutaneous edema formation.

In step 430 of the method, one or more trained machine learning or artificial intelligence computer-implemented methods described above are employed to process the data collected and stored. In one embodiment of the method, individual frames of the ultrasound images generated by the ultrasound unit 101 are assessed for learned signs of impending intravascular device failure. In some embodiments, the assessment of step 430 may include comparing each image in a video of the ultrasound to a series of prior sequential images for changes of anatomy in the image that may signify impending intravascular device failure based on the learned ultrasound features. In further embodiments, this assessment of step 430 may further include comparing each image in the video to a series of forward sequential images for changes of anatomy in the image that may signify impending intravascular device failure based on learned ultrasound features. The comparison of an image to a series of prior and/or forward sequential images helps detect subtle changes in anatomy that may not be apparent from an assessment of one individual frame. In still further embodiments, this assessment of step 430 may include analyzing both the individual frames and the series of prior and/or forward sequential images to determine learned signs of impending intravascular device failure.

In step 440 of the method, an indication is provided to a user of one or more conditions underneath the subject's skin that predict intravascular device failure. In one embodiment of the method, a report is generated indicating whether a failure of the intravascular device is predicted to occur. In some embodiments, the methods of the present disclosure may provide a user with an indication of a probability of impending intravascular device failure. In some embodiments, the method of the present disclosure may also include an indication whether a failure of the intravascular device is likely to occur within a certain time period. For example, in one embodiment, the method of the present disclosure includes indicating to the user whether a failure of the intravascular device is likely within the next 48 hours. In further embodiments, the method of the present disclosure includes indicating to the user whether a failure of the intravascular device is likely within the next 24 hours. In still further embodiments, the method of the present disclosure includes indicating to the user whether a failure of the intravascular device is likely within the next 12 hours. In yet further embodiments, the method of the present disclosure includes indicating to the user that a failure of the intravascular device has already occurred.

The methods of the present disclosure are able to detect conditions underneath the subject's skin that predict intravascular device failure before external evidence of failure and with a high degree of accuracy. For example, the methods of the present disclosure are able to detect conditions that predict intravascular device failure at least 12 hours before external evidence of failure. In another embodiment, the methods of the present disclosure are able to detect conditions that predict intravascular device failure at least 18 hours before external evidence of failure. In still another embodiment, the methods of the present disclosure are able to detect conditions that predict intravascular device failure at least 21 hours before external evidence of failure. In yet another embodiment, the methods of the present disclosure are able to detect conditions that predict intravascular device failure at least 24 hours before external evidence of failure. In further embodiments, the methods of the present disclosure are able to detect conditions that predict intravascular device failure at least 48 hours before external evidence of failure.

EXAMPLES

The following non-limiting examples illustrate various embodiments of the present disclosure. The examples are merely illustrative of the preferred embodiments of the present disclosure and are not to be construed as limiting the disclosure, the scope of which is defined by the appended claims.

Example 1: Prospective Sonographic Evaluation of Peripheral Intravenous Catheter-Associated Thrombophlebitis Materials and Methods
Study Design, Setting, and Selection of Participants
This study was a prospective observational investigation of thrombus development in PIVCs. The study was conducted at a large 1100 bed tertiary care center with an annual emergency department (ED) census of greater than 130,000 visits. The study was approved by The Institutional Review Board (IRB).

Study investigators recruited a convenience sample of ED patients meeting inclusion criteria. Patients aged at least 18 years with anticipated hospitalization of greater than 48 hours and a traditionally placed short peripheral catheter (1.16 inch) using visualization and/or palpation in the ED were eligible participants. Patients admitted to the high acuity progressive and intensive care units and those screened and approved by the principal investigator were specifically approached to increase the likelihood of meeting the minimum hospital length of stay goal of 48 hours. Patients were excluded if the PIVC was inserted with ultrasound guidance, voluntary withdrawal, cognitive impairment, and if the first sonographic assessment could not be conducted within 24 hours of PIVC placement. Informed consent was obtained for all subjects prior to enrollment in the study.

Study Procedure
After patient enrollment, researchers performed an initial assessment of the patient. Pertinent demographic and clinical data was abstracted from the electronic medical record (EMR) and included age, body mass index, admission blood pressure, admission heart rate, gender, smoking history, pre-existing medical conditions (diabetes, deep vein thrombosis history, clotting disorder, cancer) history, and anticoagulant medication history.

Figure 5:
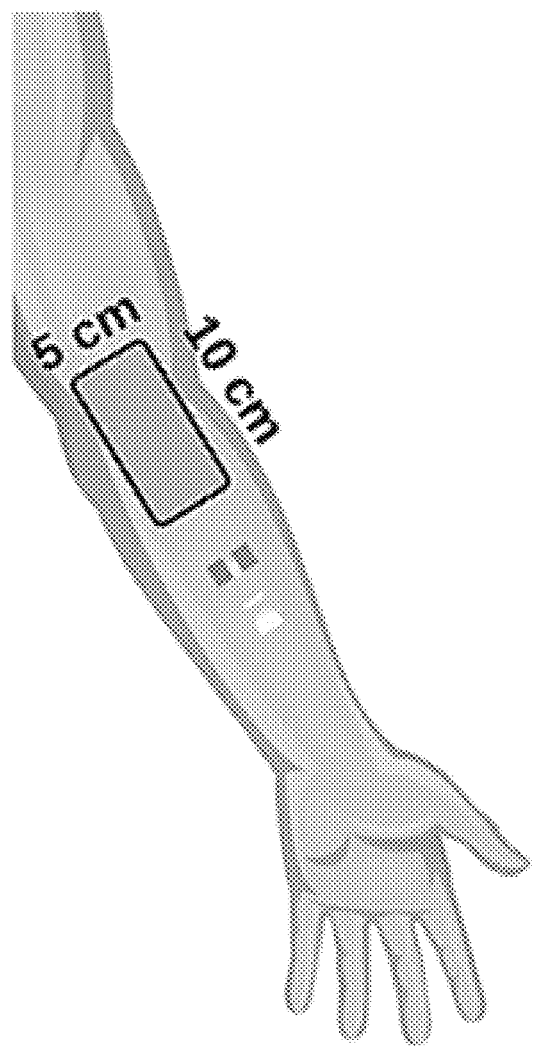
FIG. 5 illustrates an exemplary scan area of the PIVC and surrounding tissue.

Subsequently, functionality of the existing catheter was confirmed by observing blood return into the tubing upon aspiration and/or unobstructed flush with a minimum of 3 mL of normal saline flushing of the catheter. Next, the investigator performed a sonographic evaluation of the PIVC and adjacent site using a uniform scanning technique based on a previous study. Study investigators trained in using ultrasound were responsible for obtaining images. The Mindray M7 Ultrasound Machine with a 14 MHz high frequency linear array transducer was used for all sonographic evaluations. After a small amount of sterile gel was placed on the non-bordered transparent dressing proximal to the PIVC insertion site, the PIVC and surrounding tissue was scanned proximally (toward the heart) 10 cm (length)×5 cm (width) in short axis extending from the hub of the PIVC. Similar scanning was performed over the same area in the long axis. FIG. 5 demonstrates the scan area. Adequate placement of the PIVC within the vein was confirmed using ultrasound. Gel was wiped off the dressing and skin after the imaging took place.

Figure 6A:
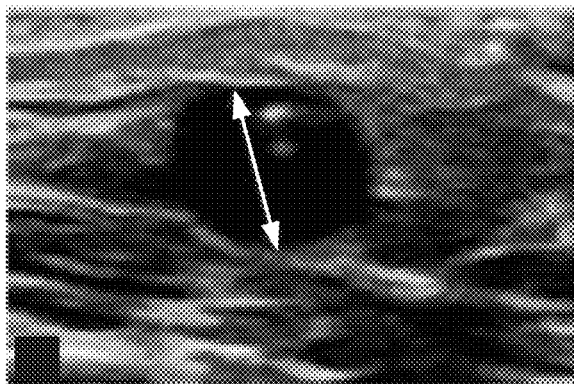
FIGS. 6A-6F illustrate measurements taken from ultrasound images according to an exemplary embodiment of the present disclosure.
Figure 6B:
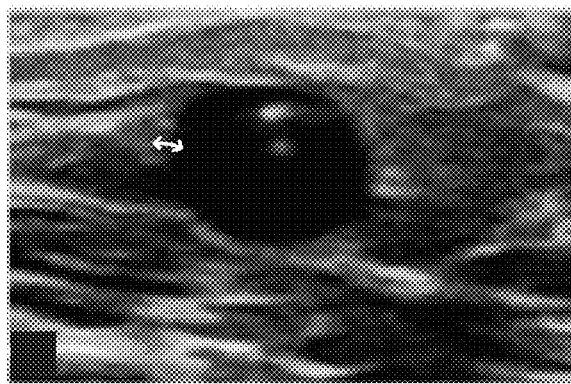
Figure 6C:
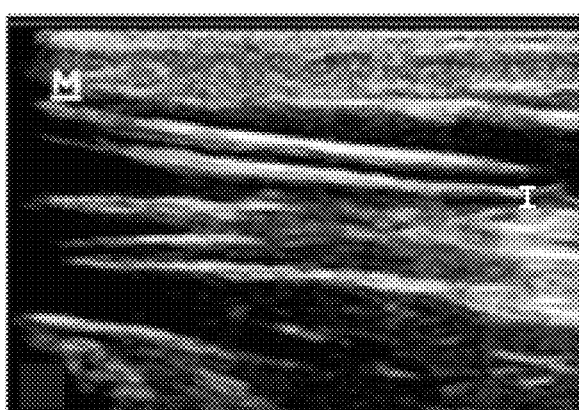
Figure 6D:
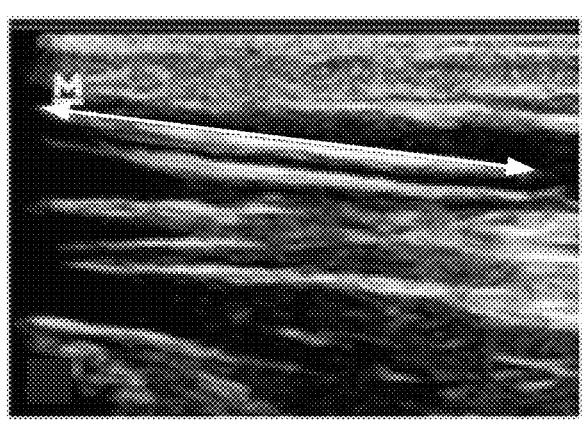
Figure 6E:
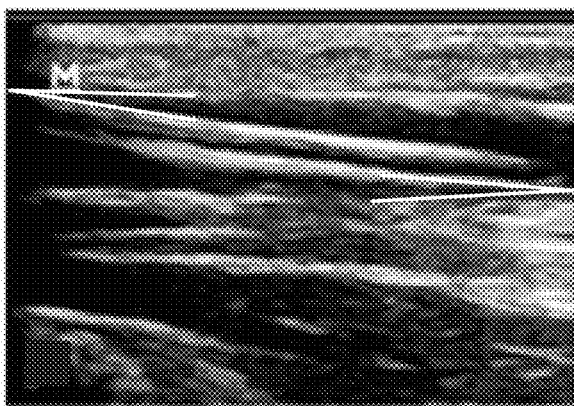
Figure 6F:
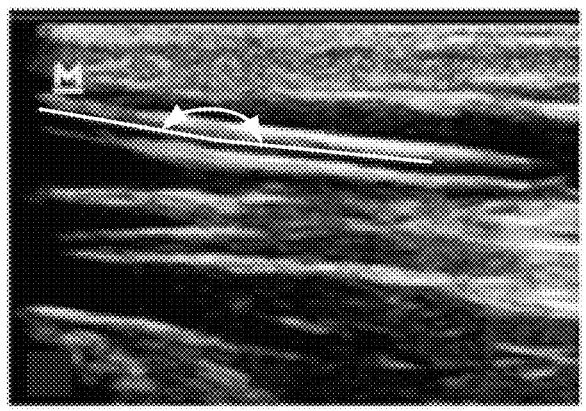
Figure 7A:
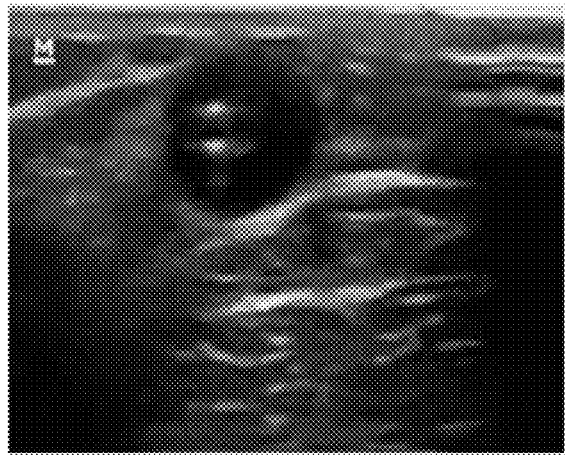
FIGS. 7A-7D illustrate ultrasound views demonstrating catheters with and without thrombus.
Figure 7B:
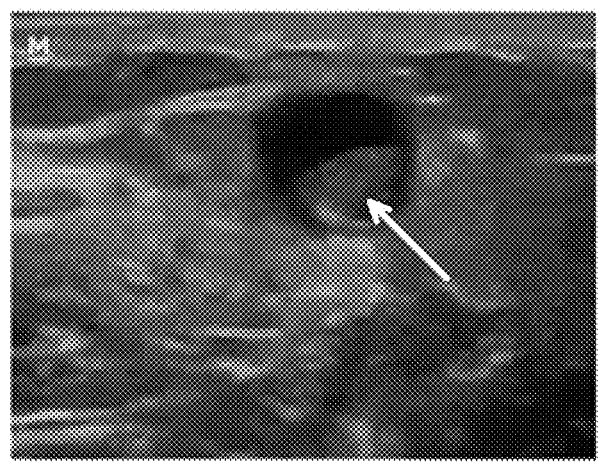
Figure 7C:
Figure 7D:
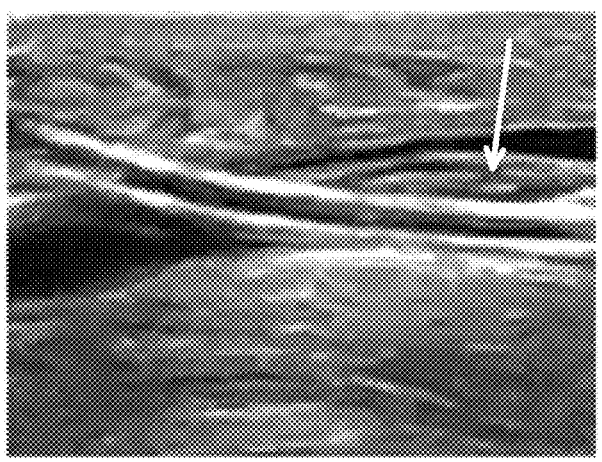

A series of cine clips (5 second duration) of the scan area were recorded. All ultrasound images were saved and archived in QPath, a secure and Health Insurance Portability and Accountability Act (HIPPA) compliant storage warehouse for review and interpretation by the Emergency Ultrasound Director. The following measurements were made by post-processing of the original images: catheter-to-vein ratio, length of catheter in vein, angle of insertion, angle of distal tip against vessel wall, vein wall thickness, distance of catheter tip to vessel wall, degree of catheter kinking, and size of thrombus formation. FIGS. 6A-6F illustrate the following measurements: vein diameter (short axis) (FIG. 6A), vein wall width (short axis) (FIG. 6B), distance of distal catheter tip to vein wall (long axis) (FIG. 6C), length of catheter in vein (long axis) (FIG. 6D), insertion angle (left) and angle of distal tip to vessel wall (right) (long axis) (FIG. 6E), and degree of kink/bend (long axis) (FIG. 6F).

Investigators performed follow-up ultrasound and clinical assessments on all catheters daily for the life of the PIVC. At each follow-up interval, the researcher documented the time of evaluation and performed a sonographic assessment using the identical method as described above for the initial assessment. These images were also saved and archived similar to the index evaluation.

Follow-up catheter functionality was assessed using a multipronged approach, including combing nursing assessments, ultrasound evaluations, and patient discussions. The follow-up ultrasound examinations further confirmed placement of the PIVC within the vein. If the investigators had any questions or concerns regarding the functionality of the PIVC, the treating nurse was brought to the bedside to reassess the PIVC with the research staff and validate the functionality of the PIVC. If the catheter failed or was removed prior to a follow-up assessment, the PIVC failure time, assessment of failure, and reason for line removal was obtained though chart review and discussion with the nursing staff when possible.

Within 24 hours of PIVC placement, ultrasound was used to assess the PIVC by measuring the diameter of the vein, length of the catheter in the vein, the angle of PIVC insertion, and the angle of the distal tip of the catheter to the vessel wall. After initial assessment of the PIVC, the PIVC and surrounding tissue were continuously monitored on a daily basis to better understand thrombus formation. Daily measurements included vein wall thickness, distance of catheter tip to vessel wall, degree of catheter kinking, as well as the assessment of thrombus or subcutaneous edema.

Ultrasound views demonstrating catheters with and without thrombus are shown in FIGS. 7A-7D.

During every ultrasound evaluation, the insertion site was examined. The participant was considered symptomatic if they received Grade 1 or greater based on the Infusion Nurses Society Phlebitis Scale, which includes the presence of erythema, pain, and/or edema at the access site. The medication administration record given through each catheter was queried for select irritant and vesicant, as defined by the Infusion Nursing Society. Frequency of administration and dosages were recorded.

Outcome Measures

The primary endpoint was to identify risk factors associated with catheter-associated symptomatic thrombus formation in PIVCs.

Statistical Rationale and Analysis

Continuous measured variables were displayed in terms of mean/average with standard deviation while categorical variables were displayed as frequencies with percentages in parentheses. Univariate, or unadjusted, analysis was performed. Continuous variables were stratified by symptomatic thrombus and compared using a Two Samples Independent T-Tests. Categorical variables also were stratified by symptomatic thrombus and compared using Chi-Square tests. Odds Ratios (OR) with corresponding 95% Confidence Intervals (95% CI) also were displayed for categorical variables (see Tables 1 and 2 below). In addition, the time to thrombus development was taken into account and compared between the various baseline variables in a time-to-event setting using univariate Cox Proportional Hazard models and displayed in terms of Hazard Ratios (HR) with corresponding 95% CI and p-values (see Table 3 below).

Multivariate/adjusted models also were generated as part of this study. Variables included in these models were chosen by all authors based on clinical rationale and the univariate/unadjusted findings. Firth's Penalized Likelihood was employed to mitigate the potential bias caused by the relatively small sample. With consideration for the time-to-thrombus development, a multivariate Cox Proportional Hazards regression model was used. Effect sizes were shown in terms of Adjusted Hazard Ratios (AHR) for the Cox model (see Table 4 below).

The $p<0.05$ indicates a statistically significant finding. All significant findings represent associations as no formal attempts were made to identify cause-and-effect, or causal, relationships. All analysis was performed in SAS 9.4 (SAS Institute Inc., Cary, NC, USA).

Results

In July and August of 2020, 77 patients were consented for the study. About 15 participants were excluded: 5 PIVCs failed and 7 patients were discharged prior to the first follow-up visit, 3 participants were excluded as two had incomplete PIVC documentation in the chart and one declined further participation. Of the 62 study subjects in the final cohort, thrombus was identified in 54 (87.10%) patients and 28 (51.85%) of the 54 patients with thrombus developed thrombus within 24 hours of PIVC placement. The mean catheter dwell time in catheters with thrombus and without thrombus was 79.94 and 52.70 hours, respectively ($p=0.0301$). Among the 54 participants that developed thrombus, 22 (40.74%) were symptomatic and 32 (59.26%) were asymptomatic. Of the 22 symptomatic cases, the number of participants with a phlebitis scale of 1 or 2 was 16 (72.73%) and 6 (27.27%), respectively.

Patient demographics, PIVC insertion details, and index measurements were similar between the symptomatic and asymptomatic thrombus groups (all $p>0.05$), as shown in Table 1 below. For continuous variables that were measured daily, including sonographic measurements, medication administration, and thrombus characteristics, there was no difference between the symptomatic and asymptomatic thrombus groups (all $p>0.05$), as shown in Table 2 below.

TABLE 1

Effect of demographic and PIVC variables on symptomatic and asymptomatic thrombosis

| | All Lines (n = 62) | Thrombus Cases (n = 54) Symptomatic (n = 22) | Asymptomatic (n = 32) | OR (95% CI) |
|---|---|---|---|---|
| Patient Demographics | | | | |
| Age of Patient (Years) | | | | |
| Mean (Standard Deviation) | 67.18 (19.25) | 61.68 (19.00) | 71.00 (18.85) | — (—, —) |
| Body Mass Index (BMI) of Patient | | | | |
| Mean (Standard Deviation) | 28.22 (6.82) | 28.92 (6.67) | 26.65 (5.38) | — (—, —) |
| Systolic Blood Pressure at Admission | | | | |
| Mean (Standard Deviation) | 131.95 (20.82) | 127.32 (19.01) | 137.09 (22.03) | — (—, —) |
| Diastolic Blood Pressure at Admission | | | | |
| Mean (Standard Deviation) | 72.61 (12.21) | 70.45 (10.82) | 74.94 (13.01) | — (—, —) |
| Heart Rate at Admission | | | | |
| Mean (Standard Deviation) | 84.56 (22.14) | 89.50 (22.84) | 82.97 (22.86) | — (—, —) |
| Gender | | | | |
| Female | 30 (48.39%) | 9 (40.91%) | 17 (53.13%) | 0.62 (0.21, 1.86) |
| Male | 32 (51.61%) | 13 (59.09%) | 15 (46.88%) | Reference Group |

TABLE 1-continued

Effect of demographic and PIVC variables on symptomatic and asymptomatic thrombosis

| | | Thrombus Cases (n = 54) | | |
| --- | --- | --- | --- | --- |
| | All Lines (n = 62) | Symptomatic (n = 22) | Asymptomatic (n = 32) | OR (95% CI) |
| History of Smoking | | | | |
| Yes | 30 (48.39%) | 12 (54.55%) | 14 (43.75%) | 1.52 (0.51, 4.52) |
| No | 32 (51.61%) | 10 (45.45%) | 18 (56.25%) | Reference Group |
| History of Diabetes | | | | |
| Yes | 17 (27.42%) | 3 (13.64%) | 10 (31.25%) | 0.39 (0.10, 1.56) |
| No | 45 (72.58%) | 19 (86.36%) | 22 (68.75%) | Reference Group |
| History of Previous DVT | | | | |
| Yes | 7 (11.29%) | 2 (9.09%) | 3 (9.38%) | 1.03 (0.16, 6.65) |
| No | 55 (88.71%) | 20 (90.91%) | 29 (90.63%) | Reference Group |
| History of Active Cancer | | | | |
| Yes | 8 (12.90%) | 5 (22.73%) | 3 (9.38%) | 2.65 (0.57, 12.4) |
| No | 54 (87.10%) | 17 (77.27%) | 29 (90.63%) | Reference Group |
| Currently on Anticoagulant Medication | | | | |
| Yes | 17 (27.42%) | 3 (13.64%) | 8 (25.00%) | 0.52 (0.12, 2.17) |
| No | 45 (72.58%) | 19 (86.36%) | 24 (75.00%) | Reference Group |
| History of Clotting Disorder | | | | |
| Yes | 8 (12.90%) | 2 (9.09%) | 4 (12.50%) | 0.77 (0.13, 4.52) |
| No | 54 (87.10%) | 20 (90.91%) | 28 (87.50%) | Reference Group |
| PIVC Insertion Variables Laterality of Successful Cannulation | | | | |
| Left | 27 (43.55%) | 9 (40.91%) | 14 (43.75%) | 0.90 (0.30, 2.69) |
| Right | 35 (56.45%) | 13 (59.09%) | 18 (56.25%) | Reference Group |
| Location of PIVC | | | | |
| Antecubital | 47 (75.81%) | 15 (68.18%) | 29 (90.63%) | 0.25 (0.06, 1.07) |
| Forearm | 15 (24.19%) | 7 (31.82%) | 3 (9.38%) | Reference Group |
| Catheter Gauge | | | | |
| 18: 1.27 mm | 12 (19.35%) | 3 (13.64%) | 7 (21.88%) | 0.61 (0.14, 2.62) |
| 20: 0.91 mm | 50 (80.65%) | 19 (86.36%) | 25 (78.13%) | Reference Group |
| Index Variables Diameter of Catheter (cm) | | | | |
| Mean (Standard Deviation) | 0.10 (0.01) | 0.10 (0.01) | 0.10 (0.02) | — (—, —) |
| Vein Diameter (cm) | | | | |
| Mean (Standard Deviation) | 0.32 (0.13) | 0.32 (0.15) | 0.36 (0.12) | — (—, —) |
| Catheter-to-vein ratio | | | | |
| Mean (Standard Deviation) | 0.36 (0.15) | 0.36 (0.17) | 0.31 (0.12) | — (—, —) |
| Length of Catheter in Vein (cm) | | | | |
| Mean (Standard Deviation) | 1.98 (0.37) | 1.98 (0.36) | 2.02 (0.35) | — (—, —) |

TABLE 1-continued

Effect of demographic and PIVC variables on symptomatic and asymptomatic thrombosis

|  | | Thrombus Cases (n = 54) | | OR (95% CI) |
|---|---|---|---|---|
|  | All Lines (n = 62) | Symptomatic (n = 22) | Asymptomatic (n = 32) |  |
| Angle of Insertion (Degrees) | | | | |
| Mean (Standard Deviation) | 15.38 (6.47) | 14.14 (5.42) | 16.91 (7.28) | — (—, —) |
| Angle Distal Tip to Vessel Wall (Degrees) | | | | |
| Mean (Standard Deviation) | 6.10 (5.13) | 6.18 (4.31) | 6.06 (5.64) | — (—, —) |

TABLE 2

Daily follow-up sonographic variables

|  | | Thrombus Cases (n = 54) | | OR (95% CI) |
|---|---|---|---|---|
|  | All Lines (n = 62) | Symptomatic (n = 22) | Asymptomatic (n = 32) |  |
| Vein Wall Thickness (cm) | | | | |
| Mean (Standard Deviation) | 0.04 (0.01) | 0.05 (0.01) | 0.05 (0.01) | — (—, —) |
| Subcutaneous Edema | | | | |
| Yes | 35 (56.45%) | 16 (72.73%) | 17 (53.15%) | 2.25 (0.71, 7.17) |
| No | 27 (43.55%) | 6 (27.27%) | 15 (46.88%) | Reference Group |
| Distance Catheter Tip to Vessel Wall (cm) | | | | |
| Mean (Standard Deviation) | 0.04 (0.04) | 0.04 (0.04) | 0.04 (0.04) | — (—, —) |
| Degree of Catheter Kinking Degrees) | | | | |
| Mean (Standard Deviation) | 4.17 (3.31) | 5.12 (2.98) | 3.98 (3.59) | — (—, —) |
| PVC Fluids Administered | | | | |
| Yes | 49 (79.03%) | 16 (72.73%) | 28 (87.50%) | 0.40 (0.10, 1.63) |
| No | 13 (20.97%) | 6 (27.27%) | 4 (12.50%) | Reference Group |
| PIVC Medication Administered | | | | |
| Yes | 51 (82.26%) | 18 (81.82%) | 27 (84.38%) | 0.82 (0.19, 3.48) |
| No | 11 (17.74%) | 4 (18.18%) | 5 (15.63%) | Reference Group |
| PVC Vesicant or Irritant Administered | | | | |
| Yes | 11 (17.74%) | 5 (22.73%) | 5 (15.63%) | 1.57 (0.40, 6.25) |
| No | 51 (82.26%) | 17 (77.27%) | 27 (84.38%) | Reference Group |
| Number of Events | | | | |
| Mean (Standard Deviation) | 4.24 (2.65) | 4.64 (2.77) | 4.22 (2.60) | — (—, —) |
| Percent of Days Idle (%) | | | | |
| Mean (Standard Deviation) | 25.84% (31.43%) | 23.84% (28.66%) | 26.38% (32.88%) | — (—, —) |
| Length of Thrombus (cm) | | | | |
| Mean (Standard Deviation) | 1.65 (0.78) | 1.74 (0.91) | 1.58 (0.68) | — (—, —) |
| Qualitative Thrombus | | | | |
| Peri/Tip | 40 (74.07%) | 16 (72.73%) | 24 (75.00%) | 0.88 (0.26, 3.02) |
| Proximal Only | 14 (25.93%) | 6 (27.27%) | 8 (25.00%) | Reference Group |
| Time to Thrombus Formation | | | | |
| <24 Hours | 28 (51.85%) | 10 (45.45%) | 18 (56.25%) | Reference Group |

TABLE 2-continued

Daily follow-up sonographic variables

| | | Thrombus Cases (n = 54) | | |
|---|---|---|---|---|
| | All Lines (n = 62) | Symptomatic (n = 22) | Asymptomatic (n = 32) | OR (95% CI) |
| 24-48 Hours | 19 (35.19%) | 10 (45.45%) | 9 (28.13%) | 1.95 (0.60, 6.37) |
| >48 Hours | 7 (12.96%) | 2 (9.09%) | 5 (15.63%) | 0.80 (0.14, 4.72) |
| Time to Thrombus Formation (Hours) | | | | |
| Mean (Standard Deviation) | 26.22 (19.88) | 26.05 (16.52) | 26.34 (22.15) | — (—, —) |
| Catheter Dwell Time | | | | |
| Mean (Standard Deviation) | 76.42 (66.60) | 87.69 (70.40) | 74.61 (70.96) | — (—, —) |

Univariate Cox models unadjusted for other factors demonstrated that participants who were on anticoagulation medication were associated with 74% lower hazard of symptomatic thrombus formation (HR: 0.26; p=0.0335). Furthermore, the average thickness of the vein wall was associated with thrombus formation; for each additional 0.01 cm of average vein wall thickness, the hazard of thrombophlebitis increased by 2.60-fold (HR: 2.60; p=0.0236) (see Table 3 below).

TABLE 3

Univariate/unadjusted hazard ratios

| Patient Demographics | HR (95% CI) | P-Value |
|---|---|---|
| Age of Patient (Years) | 0.99 (0.97, 1.00) | 0.1158 |
| Body Mass Index (BMI) of Patient | 1.02 (0.96, 1.08) | 0.5788 |
| Systolic Blood Pressure at Admission | 0.99 (0.97, 1.01) | 0.2987 |
| Diastolic Blood Pressure at Admission | 0.95 (0.90, 0.99) | 0.0183 |
| Heart Rate at Admission | 1.00 (0.98, 1.02) | 0.9707 |
| Gender | | |
| Female | 0.62 (0.27, 1.46) | 0.2755 |
| Male | Reference Group | |
| History of Smoking | | |
| Yes | 0.93 (0.40, 2.17) | 0.8651 |
| No | Reference Group | |
| History of Diabetes | | |
| Yes | 0.33 (0.10, 1.15) | 0.0826 |
| No | Reference Group | |
| History of Previous DVT | | |
| Yes | 0.98 (0.23, 4.22) | 0.9762 |
| No | Reference Group | |
| History of Active Cancer | | |
| Yes | 2.55 (0.87, 7.45) | 0.0868 |
| No | Reference Group | |
| Currently on Anticoagulant Medication | | |
| Yes | 0.26 (0.07, 0.90) | 0.0335 |
| No | Reference Group | |
| History of Clotting Disorder | | |
| Yes | 0.93 (0.22, 4.03) | 0.9247 |
| No | Reference Group | |
| PIVC Insertion Variables | | |
| Laterality of Successful Cannulation | | |
| Left | 0.73 (0.31, 1.71) | 0.4652 |
| Right | Reference Group | |

TABLE 3-continued

Univariate/unadjusted hazard ratios

| Patient Demographics | HR (95% CI) | P-Value |
|---|---|---|
| Location of PIVC | | |
| Antecubital | 0.46 (0.19, 1.13) | 0.0900 |
| Forearm | Reference Group | |
| Catheter Gauge | | |
| 18: 1.27 mm | 0.80 (0.23, 2.71) | 0.7131 |
| 20: 0.91 mm | Reference Group | |
| Index Variables | | |
| Diameter of Catheter (cm) | 0.94 (0.67, 1.32) | 0.7131 |
| Vein Diameter (cm) | 0.99 (0.96, 1.03) | 0.5723 |
| Catheter-to-vein ratio | 1.01 (0.99, 1.04) | 0.4398 |
| Length of Catheter in Vein (cm) | 0.97 (0.24, 4.02) | 0.9692 |
| Angle of Insertion (Degrees) | 0.97 (0.90, 1.04) | 0.3696 |
| Angle Distal Tip to Vessel Wall (Degrees) | 1.09 (0.99, 1.20) | 0.0749 |
| Daily Variables | | |
| Average Vein Wall Thickness (cm) | | |
| Mean (Standard Deviation) | 2.60 (1.06, 2.12) | 0.0236 |
| Subcutaneous Edema | | |
| Yes | 1.54 (0.60, 3.97) | 0.3715 |
| No | Reference Group | |
| Average Distance Catheter Tip to Vessel Wall (cm) | 1.03 (0.92, 1.15) | 0.5890 |
| Average Degree of Catheter Kinking (Degrees) | 1.08 (0.97, 1.21) | 0.1795 |
| PIVC Fluids Administered | | |
| Yes | 0.68 (0.26, 1.75) | 0.4233 |
| No | Reference Group | |
| PIVC Medication Administered | | |
| Yes | 0.98 (0.33, 2.93) | 0.9750 |
| No | Reference Group | |
| PIVC Vesicant or Irritant Administered | | |
| Yes | 2.28 (0.83, 6.27) | 0.1087 |
| No | Reference Group | |
| Number of Events | 1.04 (0.89, 1.22) | 0.6148 |
| Percent of Days Idle (%) | 0.42 (0.09, 1.88) | 0.2555 |
| Length of Thrombus (cm) | 1.15 (0.71, 1.88) | 0.5724 |
| Qualitative Thrombus | | |
| Peri/Tip | 1.04 (0.40, 2.68) | 0.9326 |
| Proximal Only | Reference Group | |

After adjusting for other factors using multivariate cox regression analysis, if >one-third (33.33%) of the vein was occupied by the catheter, it had 5.41 [(CI 1.91, 15.4) p=0.0015] times greater hazard of developing symptomatic thrombosis. Additionally, when the angle of the distal tip of the catheter to the vessel wall was >5°, the patient had 4.39 times greater hazard of developing symptomatic thrombus (p=0.0116) (see Table 4 below).

TABLE 4

Multivariate cox proportional hazards analysis

|  | AHR (95% CI) | P-Value |
|---|---|---|
| Body Mass Index (BMI) of Patient | 1.05 (0.97, 1.12) | 0.2171 |
| Catheter-to-vein ratio ≥ 33.33% | | |
| Yes | 5.41 (1.91, 15.4) | 0.0015 |
| No | Reference Group | |
| Laterality | | |
| Left | 0.59 (0.22, 1.53) | 0.2754 |
| Right | Reference Group | |
| Angle Distal Tip to Vessel Wall | | |
| ≥ 5 Degrees | | |
| Yes | 4.39 (1.39, 13.8) | 0.0116 |
| No | Reference Group | |
| Age of Patient (Years) | 0.97 (0.95, 0.99) | 0.0271 |
| Degree of Catheter Kinking (Degrees) | 1.14 (0.99, 1.30) | 0.0561 |

Discussion

Complications associated with PIVCs are poorly described in the literature with few studies using objective and reproducible tools in their assessments. This unique prospective investigation utilized an objective standard of serial ultrasonography paired with the phlebitis scale to identify symptomatic thrombosis. Demographic, clinical, and PIVC related variables were then analyzed to determine key risk factors associated with thrombophlebitis in PIVCs. In multivariate analyses, it was found that catheter-to-vein ratio and steeper angle of catheter against the vein wall increased the likelihood of this complication.

It has been established that a catheter-to-vein ratio of ≥33.33% was a key threshold to increase risk of thrombophlebitis in PIVCs. This ratio was previously described as a cut-off to decrease infiltrations, but this was the first study that reported its relevance as related to thrombosis in PIVCs. Another investigation assessing peripherally inserted central catheters identified a catheter-to-vein ratio ≥45% increased risk for venous thromboembolism. Several studies have implicated larger diameter central catheters as risk factors for thrombosis. It is postulated that this is related to the impact of the size of the catheter residing in the vein and attenuating peri-catheter blood flow velocities. As the diameter of the catheter increases, blood flow decreases and stasis propagates risk of clotting. Similar flow dynamic principles likely apply to catheters in the peripheral circulation.

There was a higher risk of thrombophlebitis in patients with a catheter tip angle of ≥5 degrees against the vessel wall. It was hypothesized that the steeper angle likely caused endothelial cell damage via mechanical irritation from both the catheter tip itself as well as infusion agents against the wall. This endothelial cell damage then triggered local inflammatory cytokine release, therefore promoting inflammation, thrombus formation, and symptomatic phlebitis. This was similar to previous findings that showed greater incidence of phlebitis in patients with an angle of ≥5.8 degrees. Furthermore, as the catheter aged over time, it began to bend, and it was found that a trend between bend of the catheter and forming symptomatic phlebitis, although this was not statistically significant. This was also consistent with an analysis of PIVCs post-removal that described a relationship between catheter curvature and occlusion.

This study highlighted that sonographically visible thrombus is a very common occurrence following PIVC placement. In this population, thrombosis occurred at a higher rate (87.10%) than previously described in the literature (60.9%). While an interesting observation, the majority of cases were asymptomatic with likely limited clinical significance. Furthermore, recent investigations in central venous catheters (CVC) suggest that in some cases the peri-catheter thrombosis represents fibroblastic sleeve (FS) formation rather than traditional catheter-related thrombus. FS is generally considered a benign and insignificant clinical finding in CVCs that occurs at a higher frequency than catheter-related thrombus. In this study, it was not specifically differentiated between peri-catheter thrombus and FS formation, so any FS formation that may have occurred was inadvertently characterized as true thrombus. Given that both the quantity and location of thrombus did not impact progression to thrombophlebitis in the study population, even if a moderate proportion of peri-catheter thrombus represented FS, the clinical significance of this finding in short peripheral catheters remains unclear and needs further investigation. Overall, while some thrombus remained clinically insignificant, it is noteworthy that 41% of participants displayed signs of thrombophlebitis (pain, redness, and/or tenderness with palpation at the PIVC site). Thrombophlebitis represents a clinically significant and highly relevant endpoint, and subsequent investigations must focus on additional features that can help predict which PIVCs will progress to symptomatic thrombosis.

While catheter insertion technique can be modified, focusing on achieving more appropriate catheter-to-vein ratios, the mechanical irritation from the steeper angle of the catheter tip against the vein wall is much more difficult to overcome given current PIVC technologies. It is possible that PIVCs need modification to enhance flexibility of the catheter to keep it away from the vessel endothelium.

In sum, the study found that the increased proportion of catheter relative to vein size and steeper catheter tip angle increased the risk of thrombophlebitis. Catheter size relative to vein size is a modifiable factor that should be considered when inserting PIVCs. Additional larger prospective investigations using objective methodologies are needed to further characterize complications in PIVCs.

Example 2: Early Recognition of Peripheral Intravenous Catheter Failure Using Serial Ultrasonographic Assessments Materials and Methods A single site prospective observational investigation was conducted at an academic tertiary care center. Adult emergency department (ED) patients who underwent traditional PIVC placement in the ED and required admission with an anticipated hospital length of stay greater than 48 hours were included. Ongoing daily PIVC assessments included clinical and ultrasonographic evaluations. The primary objective was to identify ultrasonographic PIVC site findings associated with an increased risk of PIVC failure. The secondary outcome was to determine if ultrasonographic indicators of PIVC failure occurred earlier than clinical recognition of PIVC failure.

Study Design, Setting, and Selection of Participants

This study was a prospective observational investigation of PIVC failure. The study was conducted at a large 1100 bed tertiary care center with an annual ED census of greater than 130,000 visits. The Beaumont Health Institutional Review Board (IRB) approved this study.

Study investigators recruited a convenience sample of ED patients meeting inclusion criteria. Patients aged at least 18 years with anticipated hospitalization of greater than 48 hours as well as a PIVC placed using direct visualization and/or palpation were eligible participants. Patients admitted to the high acuity progressive and intensive care units were specifically targeted to increase the likelihood of meeting the minimum hospital length of stay goal of 48 hours. Patients were excluded if they voluntarily withdrew or were cognitively impaired. If the PIVC was inserted with ultrasound guidance or if the first sonographic assessment could not be conducted within 24 hours of PIVC placement, then the patient was not eligible for enrollment. Verbal informed consent was obtained for all subjects prior to enrollment in the study.

Study Procedure

After patient enrollment, researchers performed an initial assessment of the PIVC site and abstracted data from the patient's electronic medical record (EMR). The following pertinent demographic and clinical data were abstracted from the EMR: age, body mass index, admission blood pressure, admission heart rate, gender, smoking history, pre-existing medical conditions (diabetes, deep vein thrombosis history, clotting disorder, cancer), and use of anticoagulant medications.

PIVC function was confirmed by clinical assessment (per institutional standard), in which a functional PIVC can be flushed without resistance and shows no external signs of unresolvable complication. PIVC complications include: pain, tenderness, redness, and leaking or swelling around the PIVC site. The investigator performed a sonographic evaluation of the PIVC and surrounding area using a uniform scanning technique that has been previously described in the literature. Study investigators trained in using ultrasound were responsible for obtaining images. The Mindray M7 Ultrasound Machine with a 14 MHz high-frequency linear array transducer was used for all sonographic evaluations. After a small amount of sterile gel was placed on the non-bordered transparent dressing proximal to the PIVC insertion site, the PIVC and surrounding tissue was scanned proximally (towards the heart) 10 cm (length)×5 cm (width) in short axis extending from the hub of the PIVC. Similar scanning was performed over the same area in the long axis. FIG. 5 demonstrates the scan area. Adequate placement of the PIVC within the vein was confirmed using ultrasound. Sterile ultrasound gel was cleaned off the PIVC site and skin after the imaging took place.

A series of video clips (five seconds duration) and still images of the scan area were recorded. All ultrasound data was saved and archived in QPath, a secure and Health Insurance Portability and Accountability Act (HIPPA) compliant storage warehouse for review and interpretation by the Emergency Ultrasound Director. The following measurements were made by post-processing of the original images: catheter-to-vein ratio, length of catheter in vein, angle of insertion, angle of distal tip against vessel wall, vein wall thickness, distance of catheter tip to vessel wall, degree of catheter kinking, and size of thrombus formation. The vein diameter (short axis), vein wall width (short axis), distance of distal catheter tip to vein wall (long axis), length of catheter in vein (long axis), insertion angle (left) and angle of distal tip to vessel wall (right) (long axis), and degree of kink/bend (long axis) measurements are shown in FIGS. 6A-6F.

Figure 8:
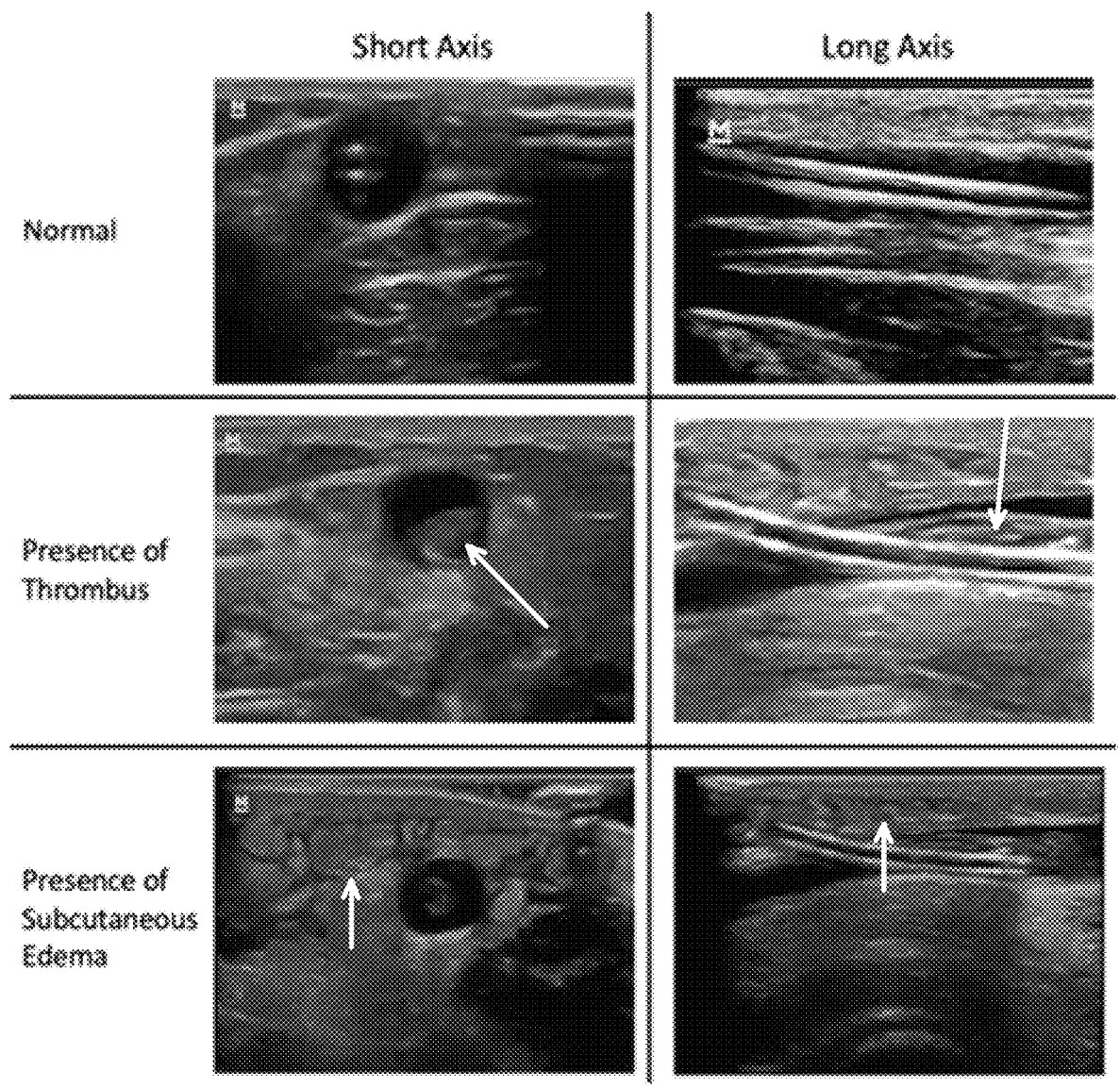
FIG. 8 illustrates ultrasound views demonstrating catheters with and without thrombus and subcutaneous edema.

Investigators performed follow-up ultrasound and clinical assessments on all catheters daily for the life of the PIVC. At each follow-up interval, the researcher documented the time of evaluation and performed a sonographic assessment using the identical method as described above. Subsequent images and videos were also saved, archived, and reviewed as described above. Follow-up ultrasound data included the additional variables: vein wall thickness, distance of catheter tip to vessel wall, degree of catheter kinking, as well as the assessment of thrombus and subcutaneous edema, as shown in FIG. 8. Subcutaneous edema was defined as presence of fluid within the subcutaneous tissue adjacent to the vein of interest. Sonographically, this appears as a cobblestone pattern.

Clinical staff document the functional status of PIVCs in the EMR as a standard of care measure within our institution. Daily assessment of catheter function was accomplished by reviewing this documentation in the EMR for any notation of catheter failure or complications. If the investigators had any questions or concerns regarding the functionality of the PIVC, clinical staff was brought to the bedside to reassess functionality of the PIVC. If the catheter failed or was removed prior to a follow-up assessment, the PIVC failure time, assessment of failure, and reason for line removal was obtained through EMR review and discussion with the nursing staff when possible.

All medications administered through each catheter were queried and cross-referenced against known irritants and vesicants, as defined by the Infusion Nursing Society. Frequency of administration and dosages were recorded. Beyond vesicants and irritants, the number of overall catheter events was also recorded. A catheter event was defined as any instance where fluid was administered through the catheter regardless of quantity or composition. However, flushing was considered a component of routine care and PIVC maintenance and was not considered an independent event.

Outcome Measures

The primary objective was to identify ultrasonographic PIVC site findings associated with an increased risk of PIVC failure. The secondary outcome was to determine if ultrasonographic indicators of PIVC failure occurred earlier than clinical recognition of PIVC failure. PIVC failure was defined as the presence of any irreversible PIVC-related complication on a traditional clinical external exam.

Statistical Rationale and Analysis

No formal sample size calculation was conducted for this investigation. Given the paucity of existing evidence on this topic, we had difficulty substantiating any assumptions and making a precise calculation. Instead, enrollment was based upon feasibility during the study period.

Continuously measured variables were displayed in terms of mean/average with standard deviation while categorical variables were displayed as frequencies with percentages in parentheses. Univariate, or unadjusted, analysis was performed. Continuous variables were stratified by PIVC failure/survival and compared using a Two Samples Independent T-Tests. Categorical variables also were stratified by PIVC failure/survival and compared using Chi-Square tests. Odds Ratios (OR) with corresponding 95% Confidence Intervals (95% CI) also were displayed for categorical variables. In addition, univariate logistic regression models were used and results were displayed in terms of Odds Ratios (OR) with corresponding 95% CI and P-Values. Kaplan-Meier Curves were graphically generated to show the difference in time-to-event outcomes on selected characteristics. Pearson's correlation and a Paired T-Test were used to assess the association between Time to Subcutaneous Edema and Time to Failure.

Multivariate/adjusted models also were generated as part of this study. Variables included in these models were chosen based on clinical rationale and the univariate/unadjusted findings. Firth's Penalized Likelihood was employed to mitigate the potential bias caused by the relatively small sample. A multivariate logistic regression model was used. Effect sizes were shown in terms of Adjusted Odds Ratios (AOR) with 95% CI and P-Values for the logistic model.

P-Value <0.05 indicates a statistically significant finding. All significant findings represent associations as no formal attempts were made to identify cause-and-effect, or causal, relationships. Data was entered and managed in RedCap and all analysis was performed in SAS 9.4 (SAS Institute Inc., Cary, NC, USA).

Results

In July and August of 2020, 77 patients consented for the study; of these, 15 participants were excluded. 12 of these patients were lost to follow up (5 PIVCs failed, and 7 patients were discharged prior to the first ultrasound evaluation). Additionally, 2 PIVCs were excluded due to incomplete clinical PIVC documentation and one patient voluntarily withdrew from the study. Of the remaining 62 PIVCs, 24 (38.7%) met the criteria for premature failure and 38 (61.2%) survived to completion of therapy. The mean catheter dwell time was 76.42 hours (SD=66.60).

Patient demographics and comorbidities were similar between the catheters that failed and survived to completion of therapy (all P≥0.05) (as shown in Table 5 below). IV Vesicant/Irritant administration was more common in catheters who failed (P=0.0064) and the average number of catheter events in the survival group was 3.39, which was significantly less than the failure group at 5.58 (P=0.0011). The average percent of days idle for the survival group was 38%, compared to 6% in the failure group (P<0.0001) (as shown in Table 6 below).

TABLE 5

| Patient Characteristics, Comorbidities, Vital Signs, Lab Values, & IV Insertion Characteristics | | | | |
|---|---|---|---|---|
| | All PIVCs (n = 62) | Failed (n = 24) | Survived (n = 38) | P-Value |
| Patient Characteristics | | | | |
| Age of Patient (Years) | | | | |
| Mean (Standard Deviation) | 67.18 (19.25) | 65.79 (18.12) | 68.05 (20.12) | 0.6561 |
| Gender | | | | |
| Male | 32 (51.61%) | 14 (43.75%) | 18 (56.25%) | |
| Female | 30 (48.39%) | 10 (33.33%) | 20 (66.67%) | 0.4178 |
| Body Mass Index (BMI) of Patient | | | | |
| Mean (Standard Deviation) | 28.22 (6.82) | 29.22 (7.26) | 27.58 (6.56) | 0.3632 |
| Comorbidities | | | | |
| History of Smoking | | | | |
| No | 32 (51.61%) | 13 (40.63%) | 19 (59.38%) | |
| Yes | 30 (48.39%) | 11 (36.67%) | 19 (63.33%) | 0.7588 |
| History of Diabetes | | | | |
| No | 45 (72.58%) | 15 (33.33%) | 30 (66.67%) | |
| Yes | 17 (27.42%) | 9 (52.94%) | 8 (47.06%) | 0.1735 |
| History of Active Cancer | | | | |
| No | 54 (87.10%) | 22 (40.74%) | 32 (59.26%) | |
| Yes | 8 (12.90%) | 2 (25.00%) | 6 (75.00%) | 0.482 |
| History of Previous DVT | | | | |
| No | 55 (88.71%) | 20 (36.36%) | 35 (63.64%) | |
| Yes | 7 (11.29%) | 4 (57.14%) | 3 (42.86%) | 0.3243 |
| Personal History of Clotting Disorder | | | | |
| No | 54 (87.10%) | 19 (35.19%) | 35 (64.81%) | |
| Yes | 8 (12.90%) | 5 (62.50%) | 3 (37.50%) | 0.1774 |
| Currently on Anticoagulant Medication | | | | |
| No | 45 (72.58%) | 18 (40.00%) | 27 (60.00%) | |
| Yes | 17 (27.42%) | 6 (35.29%) | 11 (64.71%) | 0.7676 |
| Vital Signs at Time of Admission | | | | |
| Systolic Blood Pressure at Admission | | | | |
| Mean (Standard Deviation) | 131.95 (20.82) | 126.08 (18.68) | 135.66 (21.47) | 0.0775 |
| Heart Rate at Admission | | | | |
| Mean (Standard Deviation) | 84.56 (22.14) | 98.75 (22.01) | 75.61 (17.15) | <0.0001 |
| IV Insertion Characteristics | | | | |
| Laterality of Successful Cannulation | | | | |
| Left | 27 (43.55%) | 12 (44.44%) | 15 (55.56%) | |
| Right | 35 (56.45%) | 12 (34.29%) | 23 (65.71%) | 0.4282 |
| Location of IV | | | | |
| Antecubital | 47 (75.81%) | 20 (42.55%) | 27 (57.45%) | |
| Forearm | 15 (24.19%) | 4 (26.67%) | 11 (73.33%) | 0.318 |

TABLE 5-continued

Patient Characteristics, Comorbidities, Vital Signs, Lab Values, & IV Insertion Characteristics

| | All PIVCs (n = 62) | Failed (n = 24) | Survived (n = 38) | P-Value |
|---|---|---|---|---|
| Catheter-to-vein ratio | | | | |
| Mean (Standard Deviation) Length of Catheter in Vein (long axis) (cm) | 0.36 (0.15) | 0.37 (0.16) | 0.35 (0.15) | 0.5999 |
| Mean (Standard Deviation) Angle of Insertion (long axis) (degrees) | 1.98 (0.37) | 1.95 (0.44) | 2.00 (0.32) | 0.5949 |
| Mean (Standard Deviation) Angle of Distal Tip Against Vessel Wall (long axis) (degrees) | 15.38 (6.47) | 15.00 (4.58) | 15.61 (7.43) | 0.6953 |
| Mean (Standard Deviation) | 6.10 (5.13) | 5.67 (5.28) | 6.37 (5.09) | 0.6039 |

TABLE 6

Daily IV Characteristics, Clinical Symptoms, Sonographic Findings, IV Infusate Administration, and IV Usage Characteristics

| | All Lines (n = 62) | Failed (n = 24) | Survived (n = 38) | P-Value |
|---|---|---|---|---|
| Daily IV Characteristics Vein Wall Thickness (short axis) (cm) | | | | |
| Mean (Standard Deviation) Distance of Catheter Tip to Vessel Wall (cm) | 0.04 (0.01) | 0.04 (0.02) | 0.05 (0.01) | 0.5931 |
| Mean (Standard Deviation) Degree of Catheter Kinking (long axis) (degrees) | 0.04 (0.04) | 0.03 (0.03) | 0.04 (0.05) | 0.0561 |
| Mean (Standard Deviation) Sonographic Findings Presence of subcutaneous edema | 4.17 (3.31) | 4.36 (3.28) | 4.06 (3.37) | 0.7316 |
| No | 27 (43.55%) | 4 (14.81%) | 23 (85.19%) | |
| Yes | 35 (56.45%) | 20 (57.14%) | 15 (42.86%) | 0.002 |
| Time to Edema | (n = 35) | (n = 20) | (n = 15) | |
| Mean (Standard Deviation) | 46.92 (52.32) | 39.17 (34.61) | 57.25 (69.44) | 0.366 |
| <24 Hours | 8 (22.86%) | 6 (75.00%) | 2 (25.00%) | |
| 24-48 Hours | 18 (51.43%) | 10 (55.56%) | 8 (44.44%) | 0.5333 |
| >48 Hours | 9 (25.71%) | 4 (44.44%) | 5 (55.56%) | |
| Peri/Tip Thrombus | (n = 54) | (n = 22) | (n = 32) | |
| Yes | 40 (74.07%) | 17 (42.50%) | 23 (57.50%) | 0.6941 |
| No | 14 (25.93%) | 5 (35.71%) | 9 (64.29%) | |
| Time to Thrombus | (n = 54) | (n = 22) | (n = 32) | |
| Mean (Standard Deviation) | 26.22 (19.88) | 23.57 (14.94) | 28.05 (22.71) | 0.3862 |
| <24 Hours | 28 (51.85%) | 12 (42.86%) | 16 (57.14%) | |
| 24 Hours + | 26 (48.15%) | 10 (38.46%) | 16 (61.54%) | 0.7535 |
| IV Infusate Administration IV Medication Administration | | | | |
| No | 11 (17.74%) | 1 (9.09%) | 10 (90.91%) | |
| Yes | 51 (82.26%) | 23 (45.10%) | 28 (54.90%) | 0.0661 |
| IV Vesicant/Irritant Administration | | | | |
| No | 11 (17.74%) | 9 (81.82%) | 2 (18.18%) | 0.0064 |
| Yes | 51 (82.26%) | 15 (29.41%) | 36 (70.59%) | |
| IV Usage Characteristics Catheter Dwell Time (Hours) | | | | |
| Mean (Standard Deviation) Percent of Days Idle (%) | 76.42 (66.60) | 66.85 (44.34) | 82.47 (77.42) | 0.3171 |
| Mean (Standard Deviation) | 26% (31%) | 6% (17%) | 38% (32%) | <0.0001 |

Figure 9:
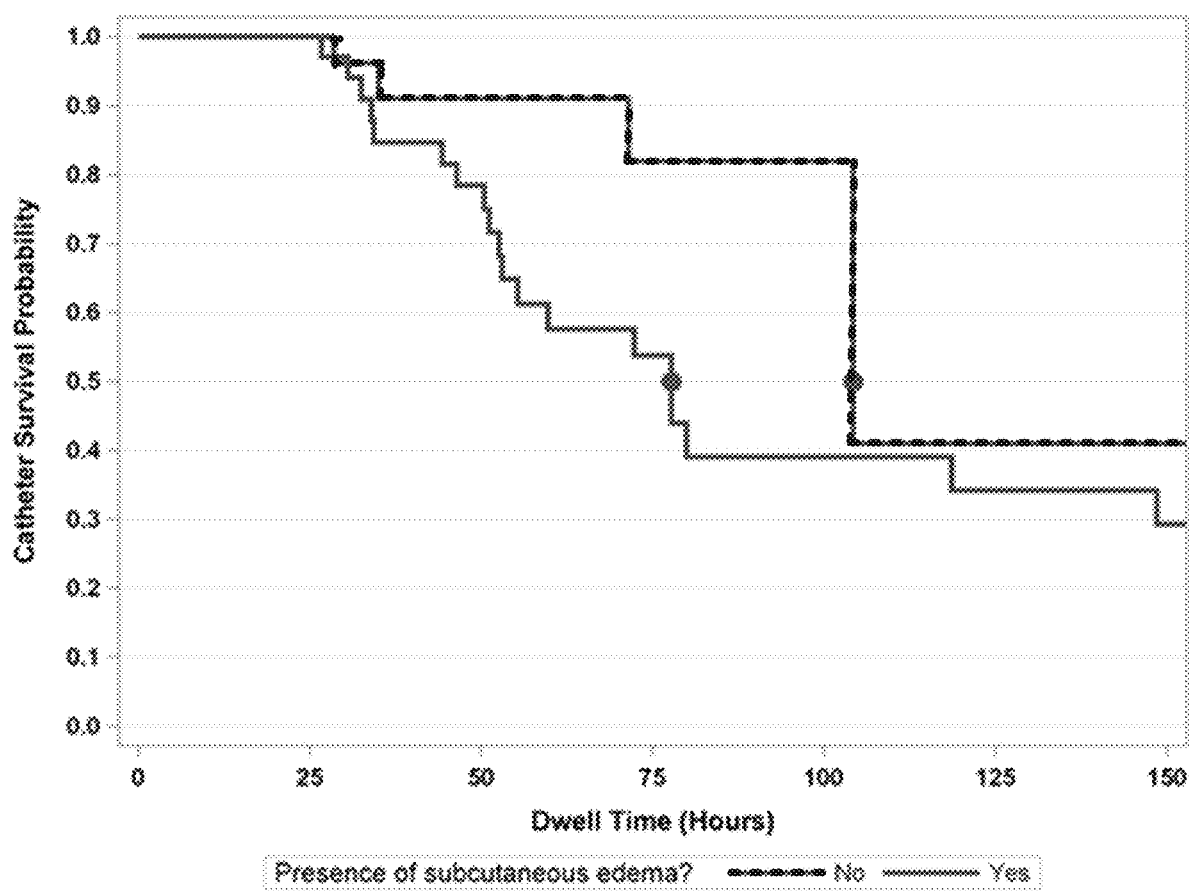
FIG. 9 illustrates Kaplan-Meier survival curve estimates for PIVC survival. This figure indicates that there is a significant association between the presence of subcutaneous edema and catheter failure, with more patients whose catheters failed presenting with ultrasonographic evidence of subcutaneous edema.

The analysis showed a significant association between ultrasonographic signs of subcutaneous edema and catheter failure. While 57.14% of PIVC's that had subcutaneous edema identified by ultrasound failed, only 14.81% of PIVC's without these findings failed (P=0.0020) (FIG. 9). Unadjusted for other factors, logistic regression analysis demonstrated that ultrasonographic subcutaneous edema was associated with 6.91-fold greater odds of catheter failure (P=0.0020). Multivariate logistic regression analysis, which was adjusted for other ultrasonographic factors, demonstrated subcutaneous edema was independently associated with 7.37-fold greater odds of premature catheter failure (P=0.0030). No other sonographic factors included in the multivariate analysis (Thrombosis, Catheter-to-Vein Ratio, Distance Catheter Tip to Vessel Wall, or Vein Wall Thickness) demonstrated significance (all P≥0.05)(as shown in Table 7 below).

TABLE 7

Univariate and Multivariate Analysis

| | Univariate | | Multivariate | |
|---|---|---|---|---|
| | OR (95% CI) | P-Value | AOR (95% CI) | P-Value |
| Patient Characteristics | | | | |
| Gender | | | | |
| Male | Reference Group | | | |
| Female | 0.65 (0.23, 1.83) | 0.4178 | | |
| Comorbidities | | | | |
| History of Smoking | | | | |
| No | Reference Group | | | |
| Yes | 0.85 (0.31, 2.37) | 0.7588 | | |
| History of Diabetes | | | | |
| No | Reference Group | | | |
| Yes | 2.20 (0.71, 6.85) | 0.1735 | | |
| History of Active Cancer | | | | |
| No | Reference Group | | | |
| Yes | 0.56 (0.11, 2.86) | 0.482 | | |
| History of Previous DVT | | | | |
| No | Reference Group | | | |
| Yes | 2.23 (0.45, 10.9) | 0.3243 | | |
| Personal History of Clotting | | | | |
| Disorder | | | | |
| No | Reference Group | | | |
| Yes | 2.86 (0.62, 13.2) | 0.1774 | | |
| Currently on Anticoagulant | | | | |
| Medication | | | | |
| No | Reference Group | | | |
| Yes | 0.84 (0.27, 2.67) | 0.7676 | | |
| IV Insertion Characteristics | | | | |
| Laterality of Successful Cannuation | | | | |
| Left | 1.52 (0.54, 4.25) | 0.4282 | | |
| Right | Reference Group | | | |
| Location of IV | | | | |
| Antecubital | Reference Group | | | |
| Forearm | 0.53 (0.15, 1.86) | 0.318 | | |
| Catheter-to-Vein Ratio | | | | |
| Ratio ≥33% | 1.23 (0.44, 3.42) | 0.6935 | 1.50 (0.44, 5.11) | 0.5165 |
| Ratio <33% | Reference Group | | Reference Group | |
| Sonographic Findings | | | | |
| Distance Catheter Tip to Vein Wall | | | | |
| 0 only | Reference Group | | Reference Group | |
| 0 and >0 | 0.80 (0.25, 2.50) | 0.6962 | 0.63 (0.17, 2.34) | 0.4929 |
| >0 only | 0.48 (0.08, 2.89) | 0.4187 | 0.47 (0.06, 3.89) | 0.4869 |
| Vein Wall Thickness | | | | |
| Thickness ≥0.04 cm | 0.62 (0.22, 1.77) | 0.3721 | 0.39 (0.11, 1.42) | 0.1528 |
| Thickness <0.04 cm | Reference Group | | Reference Group | |

TABLE 7-continued

Univariate and Multivariate Analysis

|  | Univariate | | Multivariate | |
| --- | --- | --- | --- | --- |
|  | OR (95% CI) | P-Value | AOR (95% CI) | P-Value |
| Subcutaneous Edema | | | | |
| Yes | 6.91 (2.03, 23.5) | 0.002 | 7.37 (1.97, 27.6) | 0.003 |
| No | Reference Group | | Reference Group | |
| Presence of Thrombus | | | | |
| Yes | 1.29 (0.37, 4.51) | 0.6941 | 1.76 (0.24, 13.0) | 0.5729 |
| No | Reference Group | | Reference Group | |

Among failed catheters, the etiology of failure was noted in the EMR for 20 (83.33%) of the cases. Overall, these etiologies included 3 (12.5%) dislodgement events, 6 (25%) cases of infiltration, 1 (4.16%) catheter kinking issue, 6 (25%) cases where the PIVC was leaking, 4 (16.66%) failed due to pain at the site, and in 4 (16.66%) cases the cause of failure was not documented.

While the average time to the clinical recognition of PIVC failure was 68.26 hours, the average time to ultrasonographic evidence of subcutaneous edema was only 39.17 hours in lines where we had information for time to failure and time to subcutaneous edema noted in the data (n=20). On average, edema was noted 29.09 hours before failure (P=<0.0001).

In sum, PIVC failure occurred in 24 (38.71%) participants. Multivariate logistic regression demonstrated that the presence of ultrasonographic subcutaneous edema [AOR 7.37 (1.91, 27.6) p=0.0030] was associated with an increased likelihood of premature PIVC failure. Overall, 6 (9.67%) patients had subcutaneous edema present on clinical exam, while 35 (56.45%) had subcutaneous edema identified on ultrasound. Among patients with PIVC failure, average time to edema detectable on ultrasound was 46 hours and average time to clinical recognition of failure was 67 hours (P=<0.0001).

Discussion

This is the first investigation that identifies ultrasonographic site assessment as a major potential tool in predicting impending PIVC failure. It was found that the presence of subcutaneous edema on ultrasound was a significant predictor of PIVC failure despite a normal clinical exam. It was determined that clinical exam was notably inadequate in identifying subcutaneous edema as only 6 patients experienced infiltration based on clinical assessment while 35 (56.45%) patients developed subcutaneous edema on ultrasound. Recent exploratory literature has suggested that subcutaneous edema represents more than a compromised or leaking vein due to infiltration. Instead, subcutaneous edema may represent a local inflammatory reaction due to ongoing mechanical and chemical insults to the vein wall. Strategies targeting a reduction of subcutaneous edema may improve PIVC survival.

While other sonographic variables were not associated with a higher risk of PIVC failure, some interesting associations were noted that could be considered in future investigations. Prior research has shown that the location of the PIVC tip may be a potential factor in failure. While prior work has regarded this as a static variable, the methodology described herein of serial assessments helped discover that catheter tip location varies over the device's lifespan. In 44 (71%) cases, the catheter tip to wall distance varied between daily evaluations. In 87% of cases, the catheter tip contacted the vein wall at least once during its lifespan, illustrating that vein irritation from PIVC tip likely occurs in more catheters than previously reported. Within the study's small cohort, average distance of the PIVC tip to the vessel wall approached statistical significance as a predictor of PIVC failure. Among failed catheters, the average PIVC tip to vein wall distance was 0.3 mm vs. 0.4 mm in the survival group (P=0.0561). Recent trials have implicated that mechanical irritation of the vein wall from the catheter tip is a strong predictor of ongoing venous inflammation. In an analysis on the location of catheter tip position within the vein, Murayama et al. found that contact of the tip against the vein wall was associated with subcutaneous edema on ultrasound. Another study in an animal model found that modifying the catheter within the vein to reduce contact against the vein wall led to a 40% reduction in subcutaneous edema. Our data and these findings suggest that modification of the PIVC tip position is likely another key component in reducing early catheter failure. Additionally, our observation that PIVC tip position is dynamic rather than static is a novel finding that must be considered when attempting to create solutions to improve PIVC survival. While prior interventions aimed at modifying PIVC tip position have focused on insertion technique, the research suggests that modification of the device itself may be more impactful.

Importantly, the results demonstrate that the presence of subcutaneous edema on ultrasound occurred significantly earlier than any external signs of PIVC failure. The approach of utilizing daily ultrasonographic site assessments allowed us to track the onset and progression of these sonographic changes and compare them to standard methods of PIVC site assessment. Thus, it was recognized that ultrasound findings indicative of impending failure were present nearly 30 hours earlier than our current method of PIVC site assessment. Early recognition of impending PIVC failure has enormous tangible benefits, particularly with respect to reducing treatment delays and decreasing hospital length of stay. One study noted that PIVC related complications led to a significantly increased hospital length of stay (5.9 days vs. 3.9 days) compared to patients without PIVC complications. Early identification of an impending failure before it is clinically apparent allows the treatment team to take a proactive and organized approach and plan for ongoing vascular access needs, potentially avoiding an interruption or delay in therapy.

CONCLUSIONS

Presence of subcutaneous edema on ultrasound is a strong predictor of PIVC failure. Subclinical subcutaneous edema occurs early and often in the course of the PIVC lifecycle with a predictive impact on PIVC failure that is inadequately captured on clinical examination of the PIVC site. The early timing of this ultrasonographic finding provides the clinician with key information to better anticipate the patient's vascular access needs. Further research investigating interventions to enhance PIVC survival once sonographic subcutaneous edema is present is needed.

What is claimed is:

1. A method for diagnosing conditions predictive of intravascular device failure, comprising:
    applying ultrasonic energy from an ultrasound unit to an area of a subject's skin over an insertion site of an intravascular device;
    collecting and storing data characterizing the area underneath the subject's skin, the data including at least one of an image or measurement taken by the ultrasound unit of the area underneath the subject's skin surrounding the insertion site of the intravascular device;
    applying a trained machine learning computer implemented method to process the data collected and stored, wherein the trained machine learning computer-implemented method is configured to receive and develop knowledge of ultrasound training data, the ultrasound training data comprising at least one of images or measurements from a plurality of test subjects of an area underneath the subjects' skin surrounding an insertion site of an intravascular device, and an indication, the indication comprising at least one of intravascular device failure or intravascular device success paired with the images or measurements received from the test subjects; and
    providing an indication to a user of one or more conditions underneath the subject's skin that predict intravascular device failure.

2. The method of claim 1, wherein the data collected by the ultrasound unit comprises at least one or a combination of: images of the intravascular device; images of a distance from the intravascular device to a wall of vasculature in which it is inserted; measurements of a distance between the intravascular device and the wall of vasculature in which it is inserted; measurements of a ratio of intravascular device diameter to vascular diameter; measurements of a length of intravascular device that resides within the vasculature; images of an area inside the vasculature in which the intravascular device is inserted; images of an area surrounding the vasculature in which the intravascular device is inserted; images or measurements of an angle of insertion of the intravascular device; images or measurements of an angle of a distal tip of the intravascular device against the wall of vasculature; images or measurements of a thickness of the wall of vasculature; images or measurements of a distance of the distal tip to the wall; images or measurements of a degree of catheter kinking; images or measurements of thrombus formation; and images or measurements of subcutaneous edema formation.

3. The method of claim 1, wherein the intravascular device comprises at least one of: peripheral intravenous catheter, arterial catheter, peripherally inserted central catheter (PICC), midline catheter, extended dwell catheter, central venous catheter (CVC), hemodialysis catheter, ECMO cannulation, Reboa catheter, or intra-aortic balloon pump.

4. The method of claim 1, wherein the trained machine learning computer-implemented method comprises at least one of a deep learning network or a convolutional neural network that includes a plurality of convolutional layers.

5. The method of claim 1, wherein the plurality of test subjects include subjects that experience intravascular device failure and subjects that experience successful intravascular device operation.

6. The method of claim 1, wherein the knowledge developed by the trained machine learning computer-implemented method comprises at least one of information permitting classification of types of alterations underneath the subject's skin that lead to intravascular device failure, information permitting classification of optimal placement of the intravascular device underneath the subject's skin, or information permitting classification of an optimal rotation or angle of the intravascular device underneath the subject's skin.

7. A method for diagnosing conditions predictive of intravascular device failure, comprising:
    applying ultrasonic energy from an ultrasound to an area of a subject's skin over an insertion site of an intravascular device;
    collecting and storing data characterizing the area underneath the subject's skin, the data including at least one of an image or measurement taken by the ultrasound of the area underneath the subject's skin surrounding the insertion site of the intravascular device;
    applying a trained machine learning computer-implemented method to process the data, wherein the trained machine learning computer-implemented method is configured to receive ultrasound training data, the ultrasound training data comprising at least one of images or measurements from a plurality of test subjects of an area underneath the subjects' skin surrounding an insertion site of an intravascular device;
    identifying the presence of one or more conditions underneath the subject's skin that predict intravascular device failure with the trained machine learning computer-implemented method; and
    providing an indication to a user of an impending intravascular device failure.

8. The method of claim 7, wherein the trained machine learning computer-implemented method comprises at least one of a deep learning network or a convolutional neural network that includes a plurality of convolutional layers.

9. The method of claim 7, wherein the trained machine learning computer-implemented method is configured to assess individual frames to identify the presence of the one or more conditions underneath the subject's skin that predict intravascular device failure.

10. The method of claim 7, wherein the trained machine learning computer-implemented method is configured to assess at least one of a series of forward sequential frames or a series of reverse sequential frames to identify the presence of the one or more conditions underneath the subject's skin that predict intravascular device failure.

11. The method of claim 7, wherein the intravascular device is a peripheral intravenous catheter.

12. A method for diagnosing conditions predictive of intravascular device failure, comprising:
    applying ultrasonic energy from an ultrasound unit to an area of a subject's skin over an insertion site of an intravascular device;
    generating, collecting, and storing data characterizing the area underneath the subject's skin, the data including at least one of an image or measurement taken by the ultrasound unit of the area underneath the subject's skin near the insertion site of the intravascular device, wherein the at least one image or measurement comprises at least one or a combination of: an image of the intravascular device; an image of a distance from the intravascular device to a wall of vasculature in which it is inserted; a measurement of a distance between the intravascular device and the wall of vasculature in which it is inserted; a measurement of a ratio of intravascular device diameter to vascular diameter; a measurement of a length of intravascular device that resides within the vasculature; an image of an area inside the vasculature in which the intravascular device is inserted; an image of an area surrounding the vasculature in which the intravascular device is inserted; an image or measurement of an angle of insertion of the intravascular device; an image or measurement of an angle of a distal tip of the intravascular device against the wall of vasculature; an image or measurement of a thickness of the wall of vasculature; an image or measurement of a distance of the distal tip to the wall; an image or measurement of a degree of catheter kinking; an image or measurement of thrombus formation; and an image or measurement of subcutaneous edema formation;

applying artificial intelligence to analyze the data and determine whether one or more conditions underneath the subject's skin indicate impending intravascular device failure; and providing an indication to a user of the impending intravascular device failure.

13. The method of claim 12, wherein the intravascular device comprises at least one of: peripheral intravenous catheter, arterial catheter, peripherally inserted central catheter (PICC), midline catheter, extended dwell catheter, central venous catheter (CVC), hemodialysis catheter, ECMO cannulation, Reboa catheter, or intra-aortic balloon pump.

* * * * *